US008172853B2

(12) United States Patent
Michelson

(10) Patent No.: US 8,172,853 B2
(45) Date of Patent: *May 8, 2012

(54) INSTRUMENTATION FOR CREATING AN INTERVERTEBRAL SPACE FOR RECEIVING AN IMPLANT

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1894 days.

This patent is subject to a terminal disclaimer.

(21) Appl. No.: 10/430,783

(22) Filed: May 6, 2003

(65) Prior Publication Data

US 2003/0195517 A1 Oct. 16, 2003

Related U.S. Application Data

(60) Continuation of application No. 09/768,524, filed on Jan. 23, 2001, now Pat. No. 6,565,574, which is a division of application No. 09/490,901, filed on Jan. 25, 2000, now Pat. No. 6,224,607.

(60) Provisional application No. 60/117,039, filed on Jan. 25, 1999.

(51) Int. Cl.
*A61B 17/58* (2006.01)

(52) U.S. Cl. ............................................. 606/96; 606/80

(58) Field of Classification Search .................... 606/61, 606/96–100, 79
See application file for complete search history.

(56) References Cited

U.S. PATENT DOCUMENTS

| 2,543,780 | A | * | 3/1951 | Hipps et al. | 606/86 |
|---|---|---|---|---|---|
| 3,848,601 | A | | 11/1974 | Ma et al. | |
| 3,955,558 | A | | 5/1976 | Fuisz | |
| 4,142,517 | A | | 3/1979 | Stavropoulos et al. | |
| 4,530,355 | A | | 7/1985 | Griggs | |
| 4,545,374 | A | * | 10/1985 | Jacobson | 606/61 |
| 4,744,353 | A | * | 5/1988 | McFarland | 606/96 |
| 4,985,019 | A | | 1/1991 | Michelson | |
| 5,195,526 | A | | 3/1993 | Michelson | |
| 5,195,541 | A | * | 3/1993 | Obenchain | 128/898 |
| 5,207,753 | A | * | 5/1993 | Badrinath | 606/96 |
| 5,250,055 | A | * | 10/1993 | Moore et al. | 606/148 |
| 5,313,962 | A | * | 5/1994 | Obenchain | 128/898 |
| 5,354,302 | A | * | 10/1994 | Ko | 606/104 |
| 5,484,437 | A | | 1/1996 | Michelson | |
| 5,489,307 | A | | 2/1996 | Kuslich et al. | |
| 5,496,304 | A | | 3/1996 | Chasan | |
| 5,522,899 | A | | 6/1996 | Michelson | |
| 5,571,109 | A | | 11/1996 | Bertagnoli | |

(Continued)

OTHER PUBLICATIONS

International Search Report dated Sep. 5, 2001 of International Application No. PCT/US00/01821.

*Primary Examiner* — Thomas J Sweet
*Assistant Examiner* — Mary Hoffman
(74) *Attorney, Agent, or Firm* — Martin & Ferraro, LLP

(57) ABSTRACT

A surgical instrument set for use in spinal surgery for forming a substantially quadrilateral space in the spine for implanting a spinal implant at least in part into and at least in part across a disc space between adjacent vertebral bodies and methods of use are disclosed. The instrument set includes an extended guard for providing protected access to the disc space and the adjacent surfaces of the adjacent vertebral bodies, a guide insertable into the guard, and a bone removal device insertable into said guide.

44 Claims, 30 Drawing Sheets

U.S. PATENT DOCUMENTS

| | | |
|---|---|---|
| 5,700,291 A | 12/1997 | Kuslich et al. |
| 5,722,977 A | 3/1998 | Wilhelmy |
| 5,741,253 A | 4/1998 | Michelson |
| 5,772,661 A | 6/1998 | Michelson |
| 5,797,909 A | 8/1998 | Michelson |
| RE36,020 E * | 12/1998 | Moore et al. .................. 606/144 |
| 5,947,971 A | 9/1999 | Kuslich et al. |
| 6,004,326 A | 12/1999 | Castro et al. |
| 6,017,305 A | 1/2000 | Bonutti |
| 6,042,582 A * | 3/2000 | Ray ................................ 606/61 |
| 6,056,749 A | 5/2000 | Kuslich |
| 6,063,088 A | 5/2000 | Winslow |
| 6,113,602 A | 9/2000 | Sand |
| 6,159,214 A | 12/2000 | Michelson |
| 6,174,311 B1 | 1/2001 | Branch et al. |
| 6,206,922 B1 | 3/2001 | Zdeblick et al. |
| 6,224,607 B1 | 5/2001 | Michelson |
| 6,537,320 B1 | 3/2003 | Michelson |
| 6,554,836 B2 | 4/2003 | Michelson |
| 6,565,574 B2 | 5/2003 | Michelson |
| 6,635,062 B2 * | 10/2003 | Ray et al. ....................... 606/96 |

\* cited by examiner

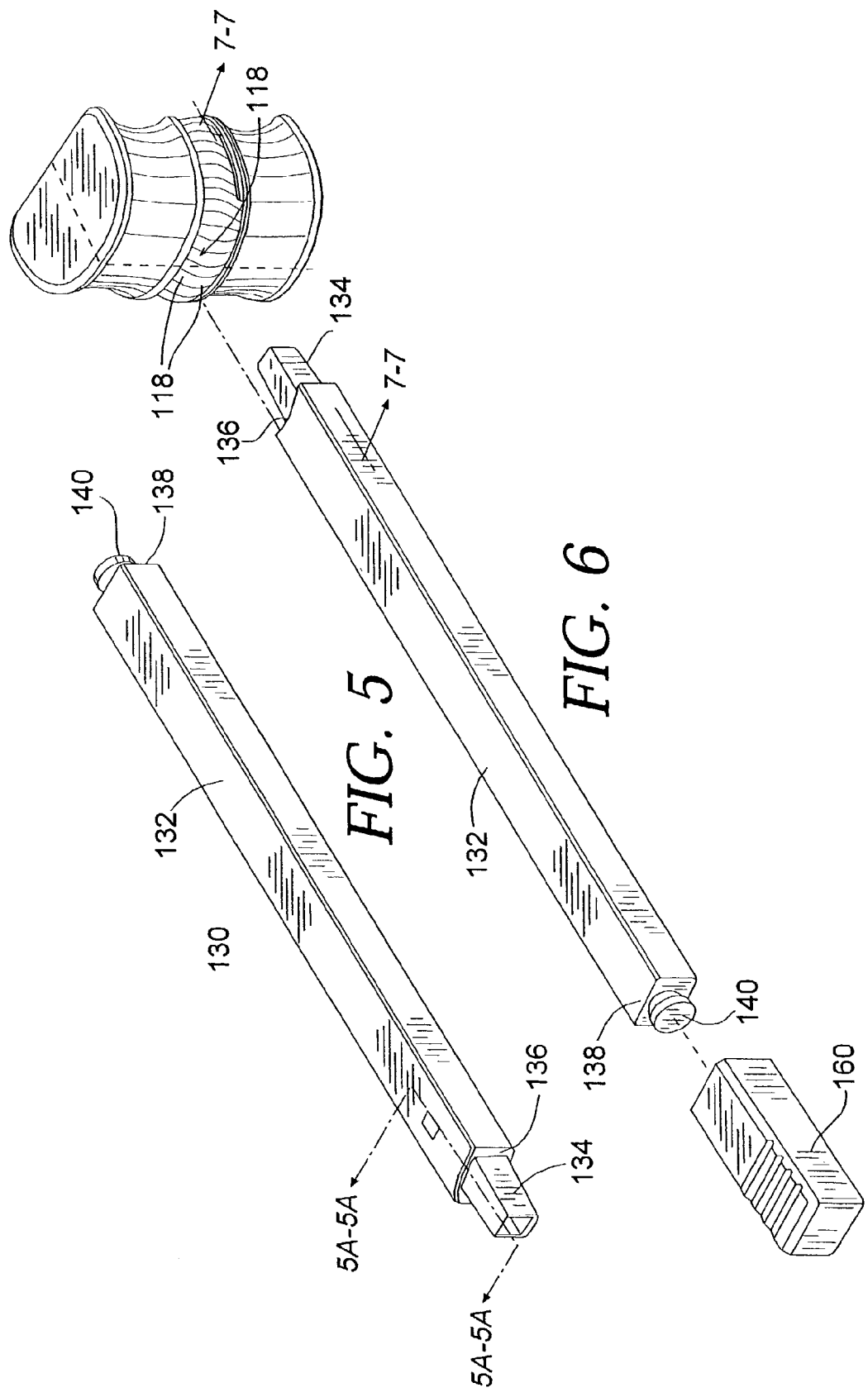

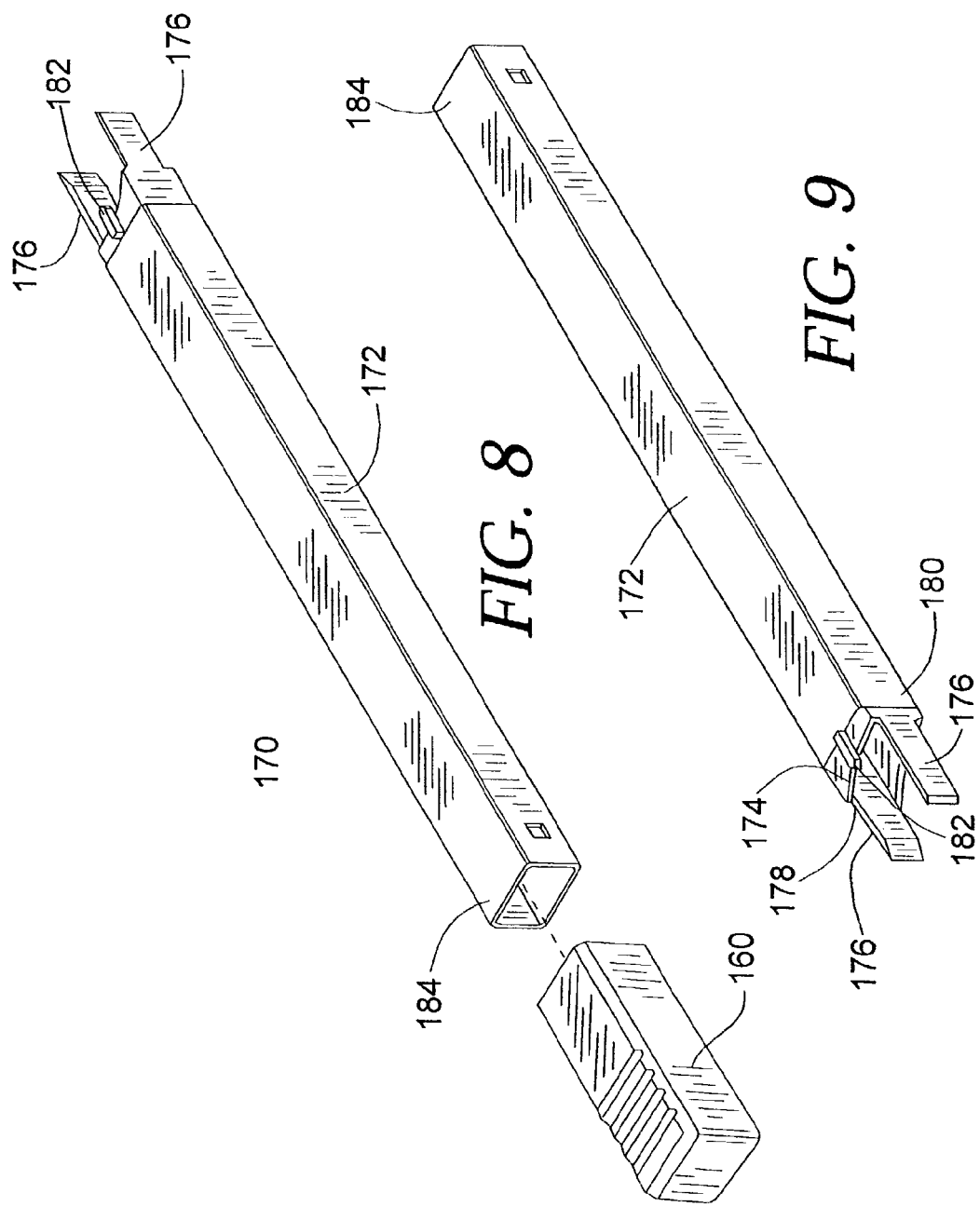

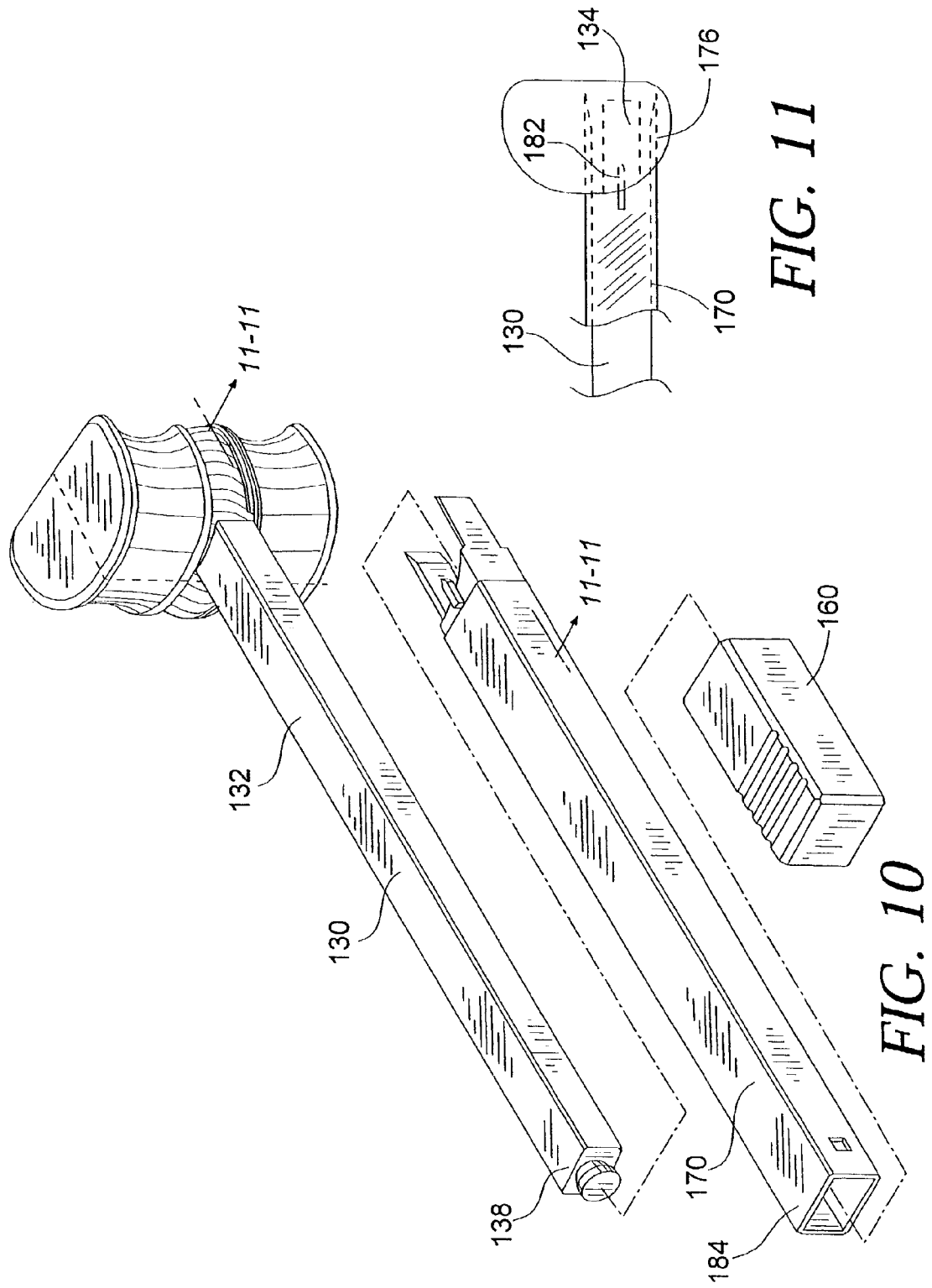

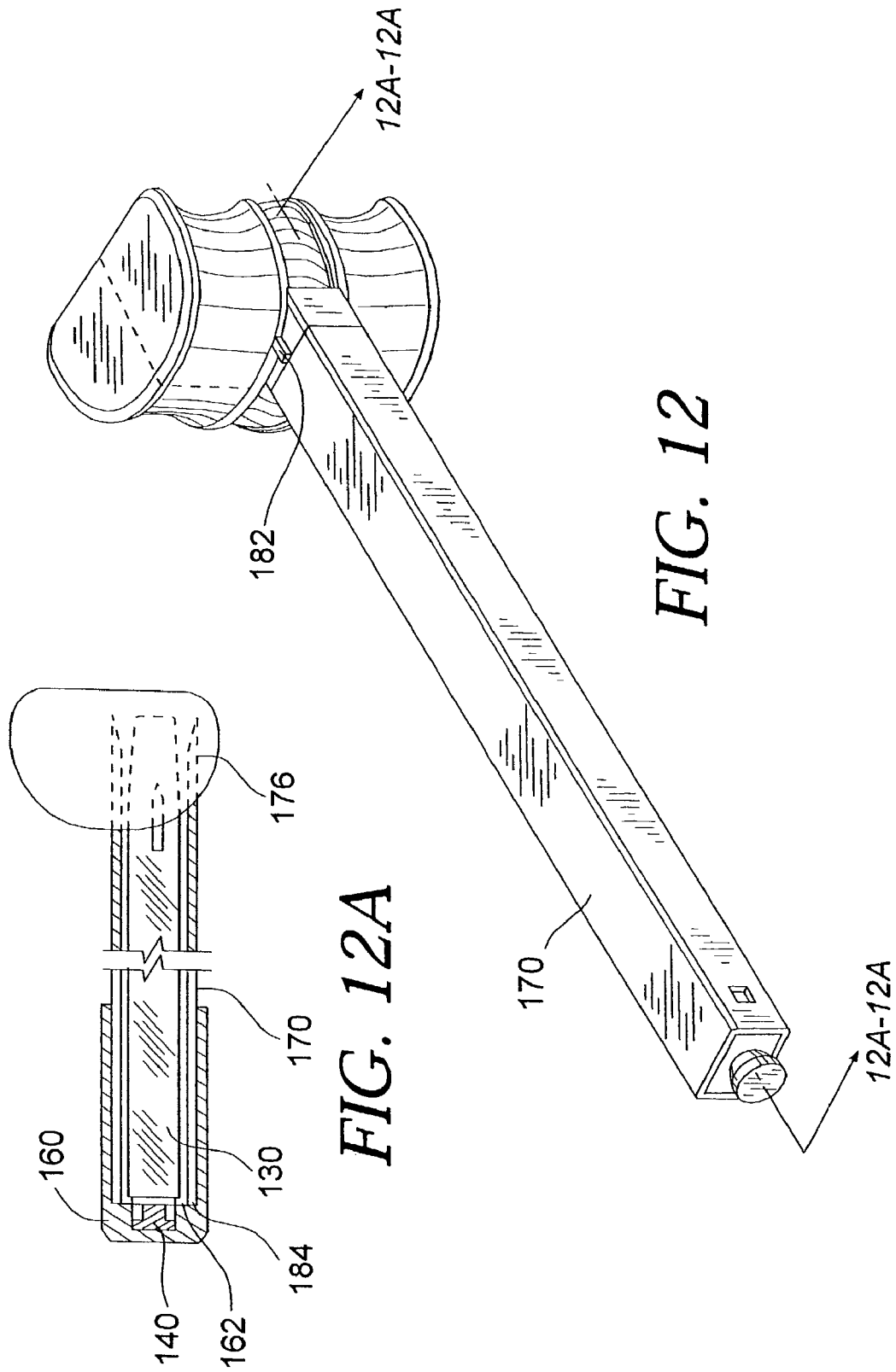

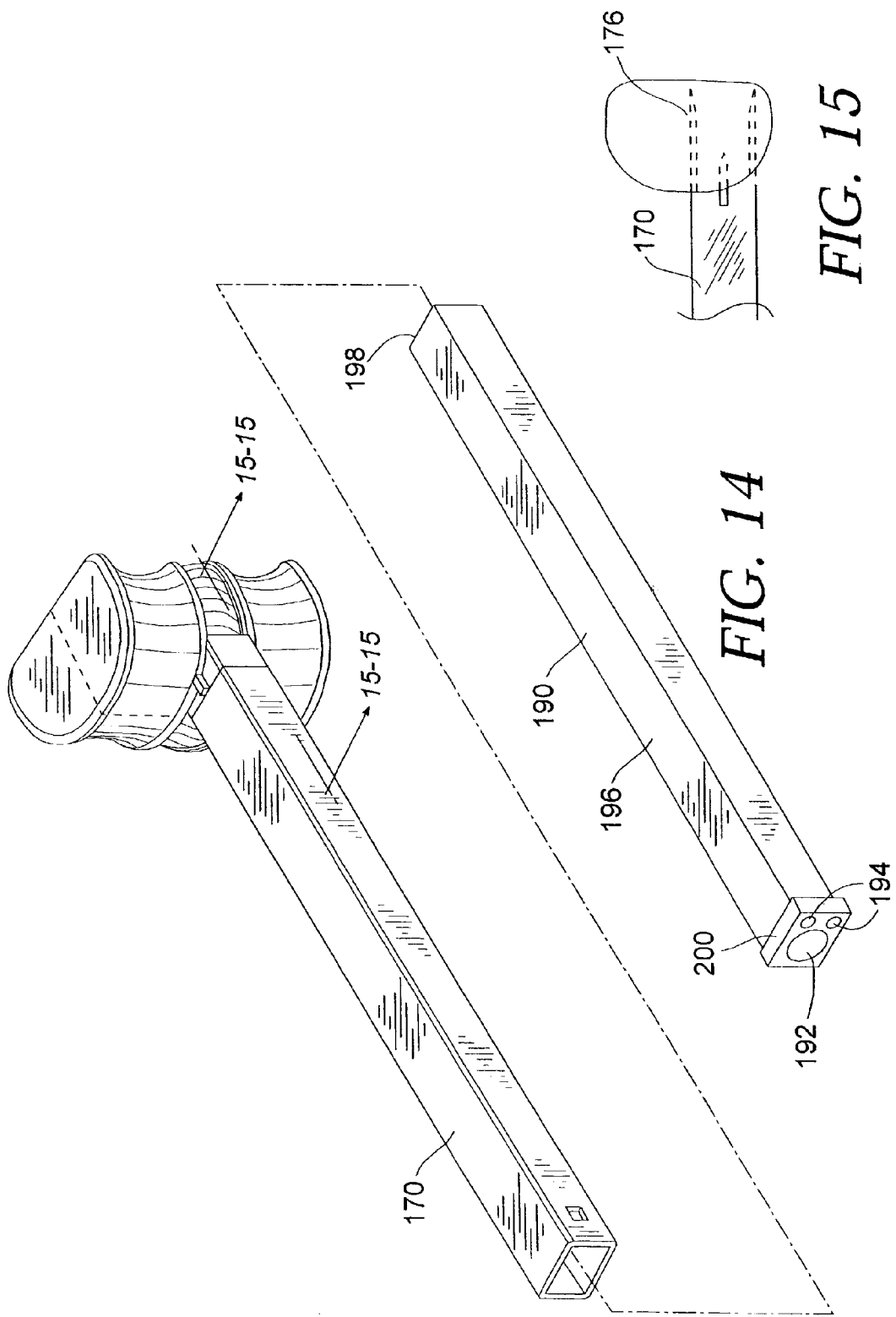

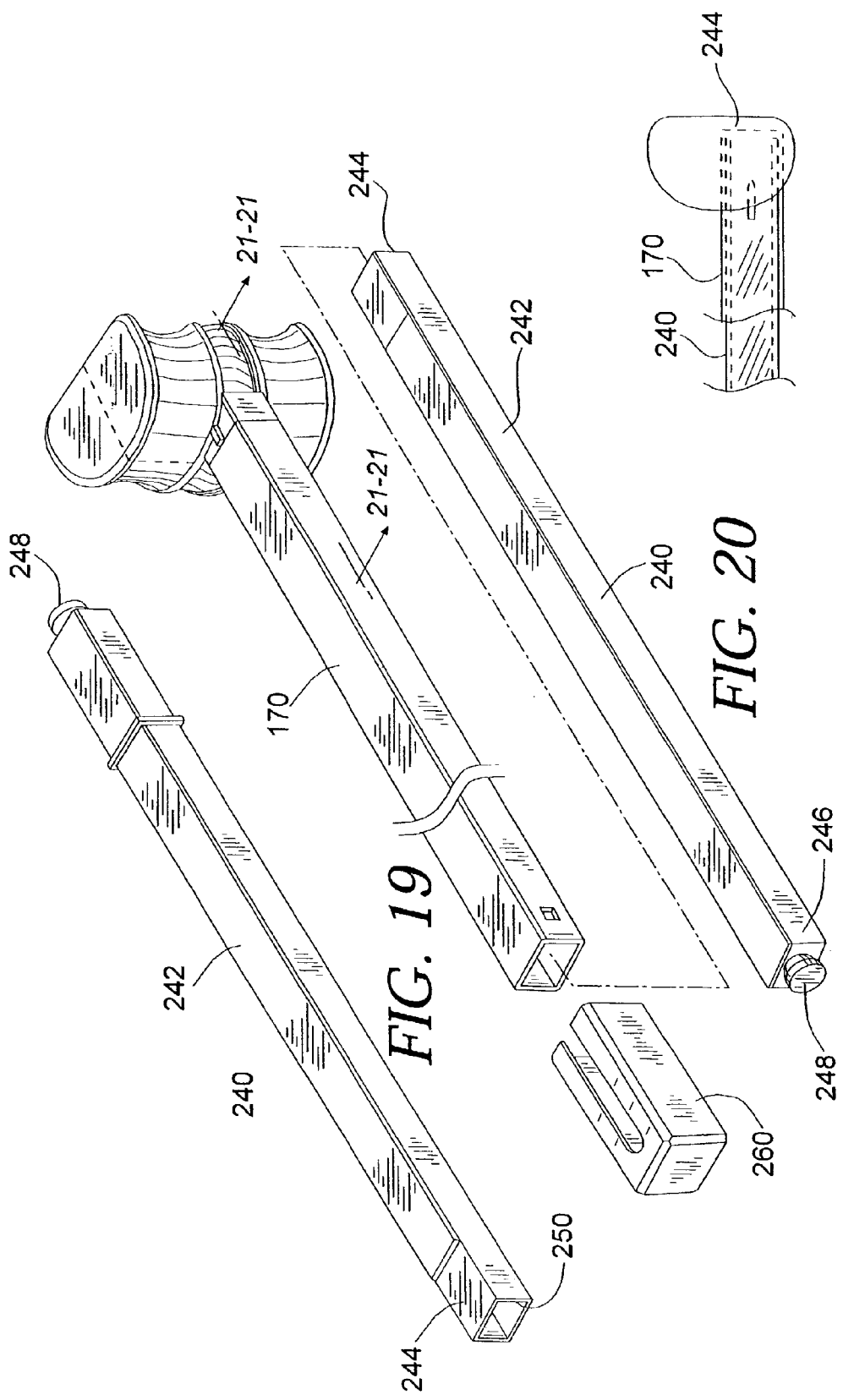

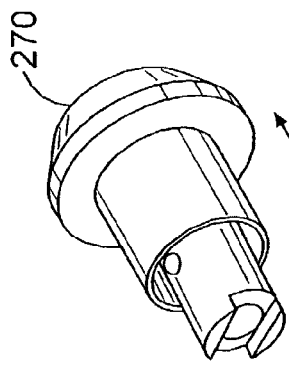
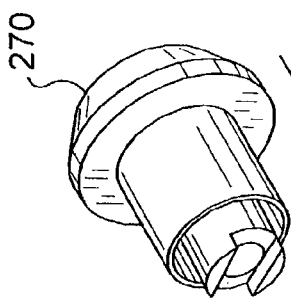
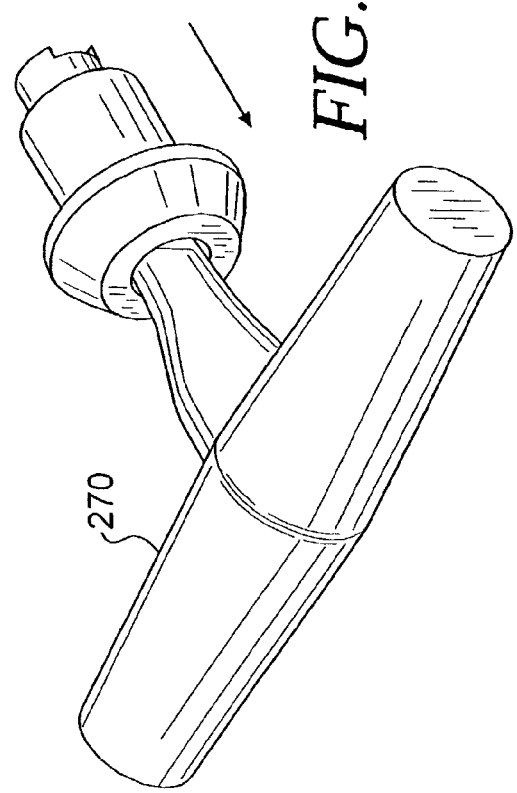
FIG. 22C
FIG. 22B
FIG. 22A

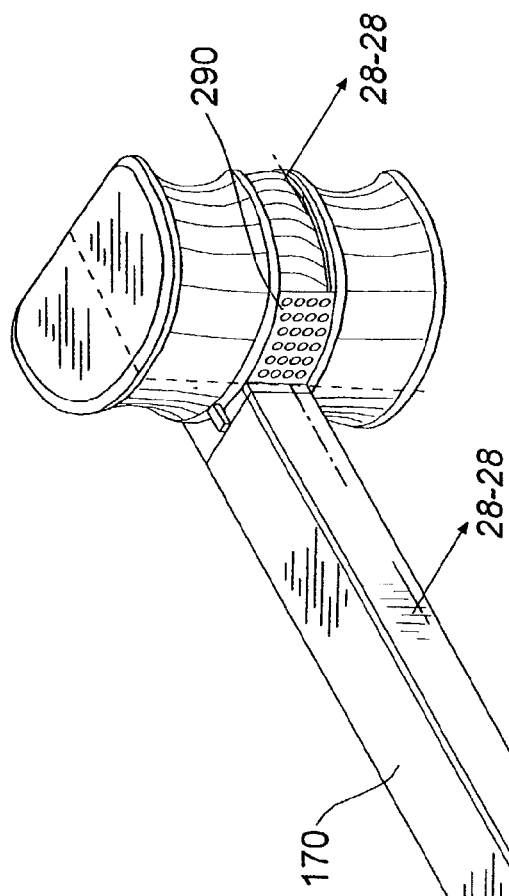

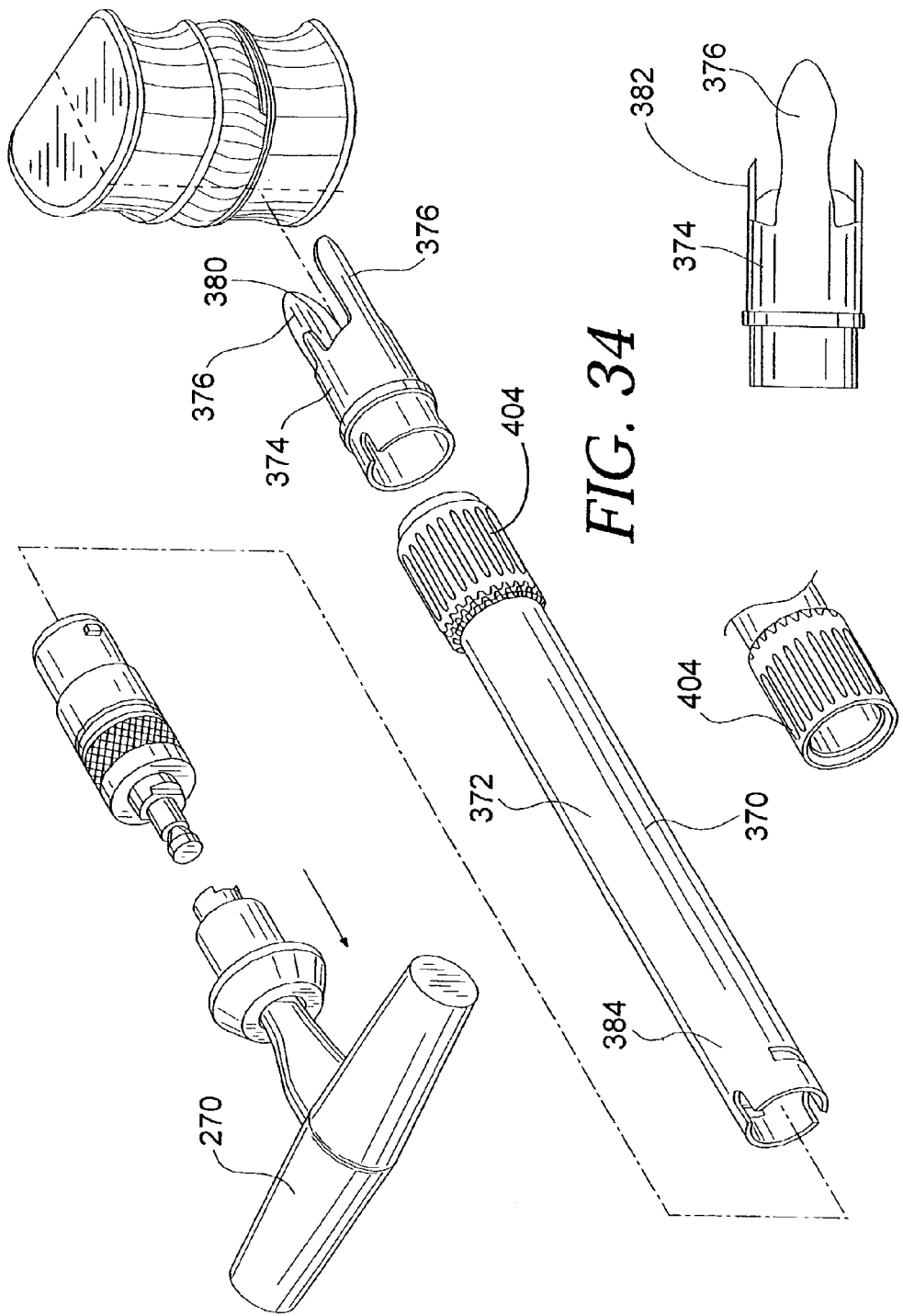

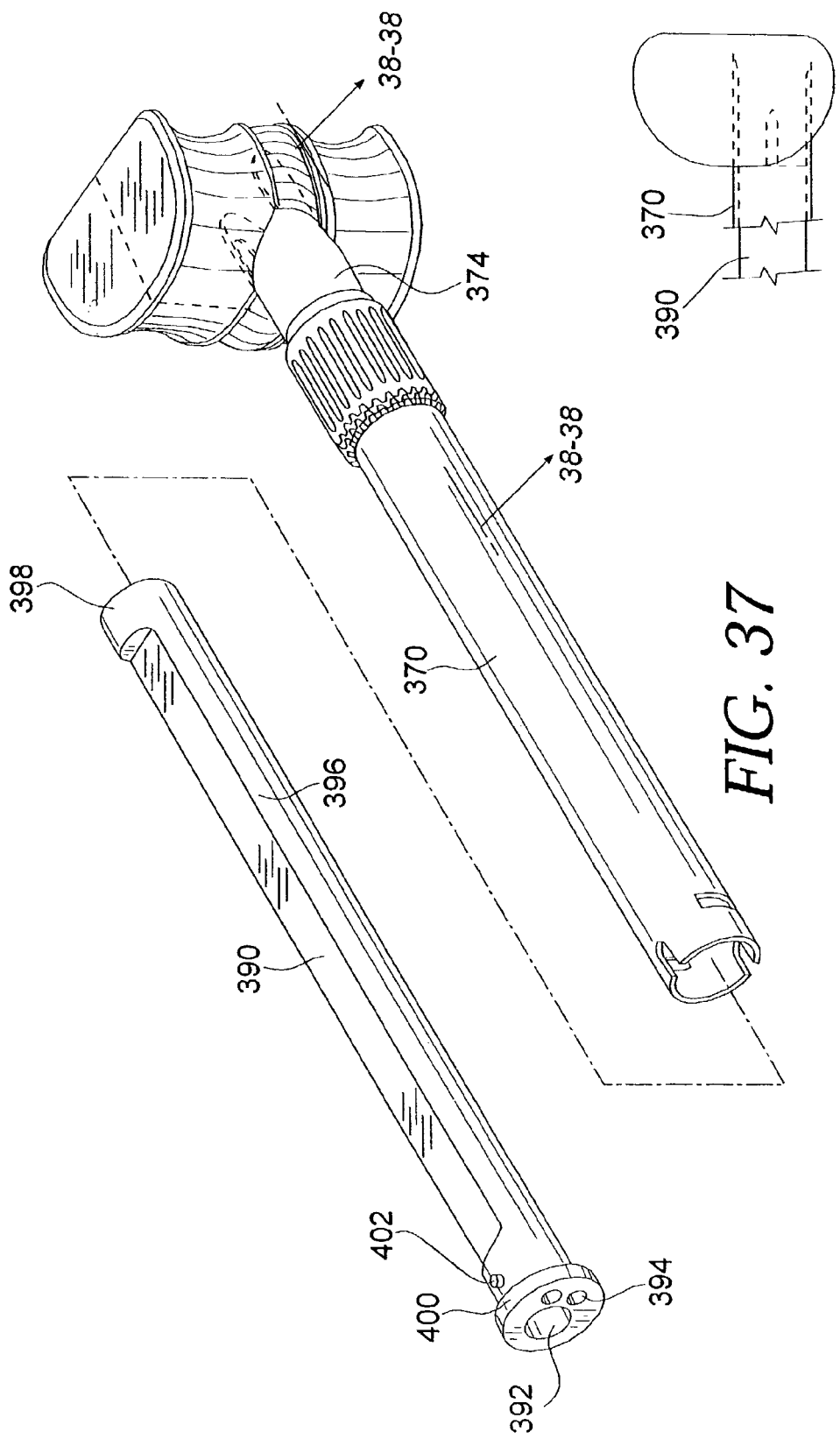

INSTRUMENTATION FOR CREATING AN INTERVERTEBRAL SPACE FOR RECEIVING AN IMPLANT

This is a continuation of application Ser. No. 09/768,524, filed Jan. 23, 2001. now U.S. Pat. No. 6,565,574, which is a divisional of application Ser. No. 09/490,901, filed Jan. 25, 2000, now U.S. Pat. No. 6,224,607, incorporated herein by reference, which claims the benefit of U.S. Provisional Application No. 60/117,039 filed Jan. 25, 1999.

BACKGROUND OF THE INVENTION

1. Field of the Invention

This invention relates generally to intervertebral spinal surgery, and more particularly to surgical instrumentation and to a method for creating one or more spaces between adjacent vertebral bodies in which the space has a shape and vertebral surfaces adapted in size to receive an implant or implants to be implanted in the space, and the method of implanting those implants.

2. Description of the Prior Art

The spinal disc that resides between adjacent vertebral bodies maintains the spacing between those vertebral bodies and, in a healthy spine, allows for relative motion between the vertebrae. With disease and/or degeneration a disc may become painful and/or mechanically insufficient warranting surgical fusion across the affected disc. Where fusion is intended to occur between adjacent vertebral bodies of a patient's spine, the surgeon typically prepares an opening at the site of the intended fusion by removing some or all of the disc material that exists between the adjacent vertebral bodies to be fused. Because the outermost layers of bone of the vertebral endplate are relatively inert to new bone growth, the surgeon must work on the endplate to remove at least the outermost cell layers of bone to gain access to the blood-rich, vascular bone tissue within the vertebral body. In this manner, the vertebrae are prepared in a way that encourages new bone to grow onto or through an implant that is placed between the vertebrae. An implant or insert may or may not promote fusion of the adjacent vertebral bodies, may be an artificial spinal disc, may permit surface ingrowth, and may be made of bone or inert material, such as titanium. All of these examples and more are implants.

Present methods of forming this space between adjacent vertebrae generally include the use of one or more of the following: hand held biting and grasping instruments known as rongeurs; drills and drill guides; rotating burrs driven by a motor; and osteotomes, chisels, and scraping implements. Surgeons often prefer a drilling technique due to its being ease, quick, and accurate. Sometimes the vertebral endplate must be sacrificed as occurs when a drill is used to drill across the disc space and deeper into the vertebrae than the thickness of the endplate. Such a surgical procedure is typically used to prepare a space in the spine for an implant having a circular cross section and necessarily results in the loss of the hardest and strongest bone tissue of the vertebrae, the endplate, and thereby robs the vertebrae of that portion of its structure best suited to absorbing and supporting the loads placed on the spine by everyday activity. Where the surgeon chooses to forego drilling a large bore across the disc space in an attempt to preserve that good bone he must nevertheless use one of the above instruments to work upon the endplates of the adjacent vertebrae to access the vascular, cancellous bone that is capable of participating in the fusion and causing active bone growth, and also to attempt to obtain an appropriately shaped surface in the vertebral bodies to receive the implant, which means and method are unreliable for that purpose.

There exists therefore a need for an improved surgical instrumentation and a related method for providing a space that is non-circular in cross section, and preferably a substantially quadrilateral space across the height of a disc space and into the adjacent surfaces of the adjacent vertebral bodies while taking advantage of the safe, easy, and accurate technique of boring or drilling into the spine to form a space and to shape the adjacent endplates to receive implants not typically associated with boring techniques.

SUMMARY OF THE INVENTION

Accordingly, it is an object of the present invention to permit the formation of a substantially quadrilateral space in a spine for inserting a spinal implant into a disc space between adjacent vertebral bodies.

Yet another object is to provide surgical instrumentation for preparing an interbody space to receive a spinal implant and a related method for working upon vertebral body endplates adjacent a disc space useful in any region of the human spine, specifically, the cervical, dorsal, or lumbar regions.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a surgical instrument set for use in spinal surgery for forming a substantially quadrilateral space in the spine for implanting a spinal implant into a disc space between adjacent vertebral bodies and the methods for doing so.

An embodiment of the present invention includes an instrument set including a spinal marker for marking a location on the spine. The marker has a shaft and a disc penetrating extension extending from the shaft for insertion into the disc space between adjacent vertebral bodies. The shaft may have any number of cross sections including rectangular and circular. The marker preferably includes a shoulder for abutting against the exterior of the adjacent vertebral bodies. The disc penetrating extension of the marker preferably is tapered to facilitate insertion into the disc space. The shaft of the marker has a proximal end and an opposite distal end oriented toward the spine. The shaft of the marker preferably includes a passage having a dye receiver at the proximal end of the shaft of the marker and at least one dye exit hole at the distal end of the shaft of the marker for marking the spine. The marker preferably includes means for coupling to a syringe.

The instrument set includes a guard having an opening for providing protected access to the disc space and the adjacent surfaces of the vertebral bodies adjacent the disc space and having a disc penetrating extension extending from the guard for insertion into the disc space between the adjacent vertebral bodies and for bearing against the adjacent vertebral endplates of the adjacent vertebral bodies. The guard may have two disc penetrating extensions extending from the guard and diametrically opposed to each other. The disc penetrating extensions preferably has a leading-edge that may include either of a pointed, tapered, radiused, chamfered, or wedge tipped shape to ease insertion of the extensions into the disc space. The guard preferably is adapted to conform at least in part to the exterior of the adjacent vertebral bodies. The guard may include a shoulder that conforms at least in part to the exterior of the adjacent vertebral bodies. The shoulder preferably curves to correspond to the external curvature of the adjacent vertebral bodies. The guard may further include means for engaging the adjacent vertebral bodies when in use. The guard includes a hollow shaft adapted to allow access through the hollow shaft to the disc space.

The instrument set further includes a guide for guiding a bone removal device. The guide has a shaft adapted for insertion into the guard. The guide includes means for guiding the formation of the substantially quadrilateral space across the height of the disc space and into the adjacent surfaces of the adjacent vertebral bodies. The guiding means preferably includes a plurality of guide bores. The plurality of guide bores may overlap one another. The plurality of guide bores may include three guide bores, and in particular may include a main guide bore and two secondary guide bores located to a side of the main guide bore. The main guide bore and the two secondary guide bores preferably are oriented such that the bores formed in the spine through the main guide bore and the two secondary guide bores form a first hole pattern, which when the guide is rotated 180 degrees and used to form a second hole pattern, the overlapping first and second hole patterns form the substantially quadrilateral space.

Another embodiment of the present invention further includes a secondary guide having a shaft adapted to be inserted into the guard. The secondary guide preferably includes means for guiding the formation of a bore centrally oriented within the space to be formed. The centrally oriented bore preferably contacts opposite sides of the substantially quadrilateral space to be formed. The instrument set may also include a bone compactor having a shaft adapted for insertion into the guard. The shaft terminates in a compaction end. The compaction end preferably has an upper surface and a lower surface that presses upon the adjacent vertebral endplates of the adjacent vertebral bodies. The compaction end preferably has either a rectangular, trapezoid, or quadrilateral cross-section, or any other shape corresponding to the desired cross-section of the space to be formed in the spine. The compaction end may be any of beveled, radiused, or tapered to ease introduction of the bone compactor into the space. The bone compactor may have a trailing end having a dimension greater than the shaft to prevent over penetration of the bone compactor into the guard. Alternatively, the instrument set may include a tool having a sharpened leading end so as to formalize the flattening of the vertebral surfaces.

An embodiment of the invention also comprises a method for creating a substantially quadrilateral space in a spine for inserting a spinal implant into a disc space between adjacent vertebral bodies, comprising the steps of: positioning a guard into contact with the adjacent vertebral bodies for protecting access to the disc space and the adjacent vertebral bodies; and boring, through the guard, a plurality of bores across the disc space to form the substantially quadrilateral space across the height of the disc space and generally into the adjacent surfaces of the adjacent vertebral bodies, rather than deep into the vertebral bodies themselves.

An embodiment of the present invention may include the step of marking the spine for guiding, by reference marks, the proper location of the guard. The step of marking preferably includes inserting a penetrating extension of a spinal marker into a central point of the disc space between the adjacent vertebral bodies. An embodiment of the present invention includes the step of placing dye spots on the spine by injecting the dye through openings in a shaft of the spinal marker. The depth of penetration of the marker into the disc space is controlled.

An embodiment of the method of the present invention includes the step of distracting the disc space between adjacent vertebral bodies, and in particular, the distracting step may include the step of inserting a distractor having a disc penetrating extension into the disc space between adjacent vertebral bodies and against endplates of the adjacent vertebral bodies. The depth of penetration of the distractor into the disc space is preferably controlled. The method may further include the step of changing disc penetrating extensions of the distractor in accordance with a desired distractor distance between adjacent vertebral bodies. The guard may be inserted over the distractor in the disc space, and then the distractor may be removed from within the guard.

The positioning step may include inserting at least one disc penetrating extension extending from the guard into the disc space between the adjacent vertebral bodies for bearing against endplates of the adjacent vertebral bodies. The insertion of the disc penetrating extension into the disc space in one embodiment of the preferred invention distracts the adjacent vertebral bodies. Another method of the present invention further includes the step of controlling a depth of penetration of the extension into the disc space. Another embodiment of the present invention includes the step of engaging the guard with the adjacent vertebral bodies through prongs extending from the guard and into the adjacent vertebral bodies.

The boring step may include the sub-step of using a template in association with the guard. The template may be rotated 180 degrees along its longitudinal axis. The boring step may include the sub-step of using either of a drill, mill, laser, burr, grinder, or other means to bore the plurality of bores. The plurality of bores may overlap. The boring step may include forming at least three bores in the spine to form a first bore pattern, and in particular may include forming at least a main bore and at least two secondary bores located to a side of the main bore. The main bore has a diameter that is preferably greater than a diameter of each of the two secondary bores. The main bore in the spine is preferably positioned to form a portion of three sides of the substantially quadrilateral space formed in the spine. Each of the two secondary bores are preferably positioned to form a portion of two adjacent sides of the substantially quadrilateral space formed in the spine. A second bore pattern having at least three bores in the spine may be formed such that the first and second bore patterns defined the substantially quadrilateral space. The substantially quadrilateral space may be one of a substantially rectangular shape and a substantially trapezoidal shape. Further a central bore can be utilized to increase the width of the space formed. The described "quadrilateral space" is defined to cover a space that is actually a generally flat upper and flat lower surface having a height therebetween that is symmetrical from side to side and that may be uniform from front to back or may be such that these opposed surfaces are in angular relationship to each other from front to back; to the extent that the sides of the space are located within the disc space and not the bone of the vertebral bodies their specific shape is not important, and need not be planar.

Further the invention may comprise the step of inserting a multiple passage drill guide into the guard to guide the formation of those bores. The guide may be inserted into the guard for guiding the forming of the first bore pattern. The invention may further include the steps of removing the guide from the guard, rotating the guide 180 degrees along its longitudinal axis, reinserting the guide into the guard, and forming, through the plurality of openings in the guide, a second bore pattern, the first and second bore patterns defining the substantially quadrilateral space. The invention may further include the step of controlling the depth of penetration of the guide into the guard.

Yet another embodiment of the present invention includes the step of compressing outer edges of the substantially quadrilateral space. The step of compressing preferably includes inserting a compactor having a compaction end through the guard and into the substantially quadrilateral space formed in the spine. The step of compressing may also include inserting a bone chisel compactor having a sharpened cutting edge for cutting bone. The depth of penetration of the compactor into the disc space is preferably controlled. The step of compressing may include the sub step of inserting a spinal implant through the guard and into the substantially quadrilateral space formed in the spine to compress the outer edges on the substantially quadrilateral space.

Another embodiment of the present invention includes a surgical method to prepare a segment of a human spine having a disc and two vertebrae adjacent the disc to receive an implant that, by way of example and not limitation, may be for fusion between body portions of the adjacent vertebrae and through the space previously occupied by the disc, each of the adjacent vertebrae to be fused including a vertebral body having an endplate outer surface adjacent the disc space, and a subchondral zone immediately internal to each endplate, the method comprising: positioning a guard into contact with the adjacent vertebral bodies for protecting access to the disc space and the adjacent vertebral bodies; and forming, through the guard, a plurality of bores to form a substantially quadrilateral space in the spine across the height of the disc space and into the adjacent endplates of the vertebrae adjacent the disc space, the quadrilateral space being formed by the removal of at least bone from at least the adjacent endplates as deep as with, and generally not deeper than, the subchondral zone of each of the adjacent endplates.

It is understood that both the foregoing general description and the following detailed description are exemplary and exemplary only, and are not restrictive of the invention as claimed.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings:

FIG. 3 is a trailing end side perspective view of the midline spinal marker of the present invention being inserted at the anterior vertebral midline into the disc space between adjacent vertebral bodies of a segment of the spine;

FIG. 5 is a leading end side perspective view of a spinal distractor of the present invention;

FIG. 6 is a trailing end side perspective view of the distractor of FIG. 5 with an impaction cap for driving the distractor into the disc space lateral to the midline (identified by reference mark) between the adjacent vertebral bodies of the spine;

FIG. 8 is an exploded trailing end side perspective view of a guard providing protected access to the disc space and the adjacent surfaces of the vertebral bodies and an impaction cap of the present invention;

FIG. 9 is a leading end side perspective view of the guard of FIG. 8;

FIG. 10 is an exploded trailing end side perspective view of the guard of FIG. 8 for insertion over the distractor of FIG. 5 shown inserted in the disc space between two adjacent vertebral bodies and a corresponding impaction cap for seating the guard into the disc space;

FIG. 11 is a cross-sectional view along lines 11-11 of FIG. 10 showing the guard inserted over the distractor in the disc space between the adjacent vertebral bodies on one side of the vertebral midline;

FIG. 12 is a trailing end side perspective view of a guard positioned over the distractor and seated after impaction to the distractor by the impaction cap into the disc space and adjacent vertebral bodies on one side of the vertebral midline;

FIG. 12A is a longitudinal cross-sectional view along 12A-12A of FIG. 12 illustrating the guard positioned over the distractor and seated after impaction to the distractor by the impaction cap into the disc space and adjacent vertebral bodies on one side of the vertebral midline;

FIG. 14 is an exploded trailing end side perspective view of a drill guide (template) of the present invention for guiding a drill for insertion into the guard;

FIG. 15 is a cross-sectional view along lines 15-15 of FIG. 14 illustrating the guard of the present invention on one side of the vertebral midline;

FIG. 19 is a leading end side perspective view of a bone compactor of the present invention;

FIG. 20 is an exploded trailing end side perspective view of the compactor of FIG. 19 for insertion within the guard shown engaging the spine and inserted in the disc space between two adjacent vertebral bodies with an impaction cap for advancing the compactor into the disc space;

FIG. 21 is a cross-sectional view along lines 21-21 of FIG. 20 illustrating the compactor placed within the guard inserted into the disc space on one side of the vertebral midline;

FIG. 22A is a trailing end perspective view of a universal handle assembly of the present invention;

FIG. 22B is a leading end perspective view of the engagement mechanism of the handle of FIG. 22A shown in the locked position;

FIG. 22C is a leading end perspective view of the engagement mechanism of the handle of FIG. 22A shown in the unlocked position;

FIG. 27 is a side perspective view of the operated segment of the spine with the guard removed having a first implant inserted on one side of the midline and between and in part into the adjacent vertebral bodies in the space created by the instrumentation and method of the present invention and with the guard inserted on the opposite side of the vertebral midline next to the implant;

FIG. 28 is a cross-sectional view along lines 28-28 of FIG. 27 illustrating the implant positioned on one side of the vertebral midline in the space created by the instrumentation and method the of the present invention and the guard inserted in the disc space on the opposite side of the vertebral midline and next to the implant;

FIG. 34 is an exploded trailing end side perspective view of a second embodiment of the guard of the present invention for placement into a segment of the spine having a removable insertion end and an adapter and a handle assembly;

FIG. 35 is a side elevational view of the removable insertion end having extended portions with an anatomical configuration;

FIG. 36 is a fragmentary view of the leading end of the guard of FIG. 34;

FIG. 37 is an exploded trailing end side perspective view of the guard of FIG. 34 inserted in the disc space between two adjacent vertebral bodies for receiving a drill (template) guide of the present invention;

FIG. 38 is a cross-sectional view along lines 38-38 of FIG. 37 illustrating the guard inserted into the disc space between two adjacent vertebral bodies on one side of the vertebral midline;

DETAILED DESCRIPTION OF THE DRAWINGS

Reference will now be made in detail to the present preferred embodiment of the invention, as illustrated in the accompanying drawings.

Figure 49:
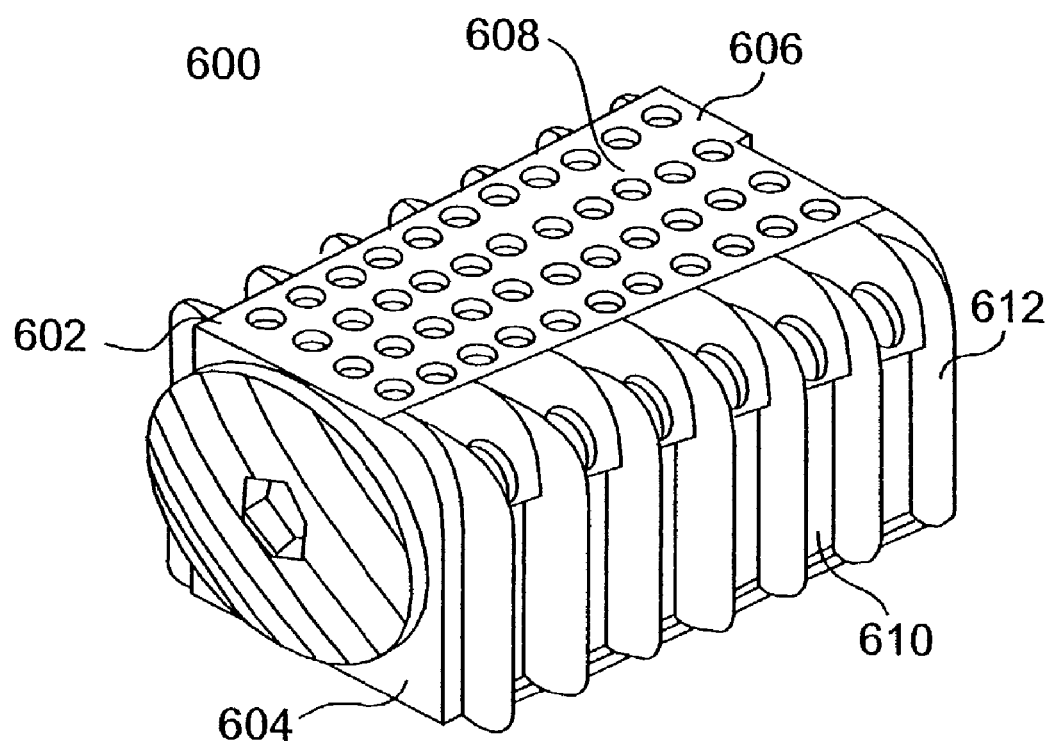
FIG. 49 is a perspective view of a spinal fusion implant oriented in an initial insertion position and configured for clockwise rotation within the disc space, the top and bottom walls thereof being tapered relative to one another for inducing angulation of the adjacent vertebral bodies.
Figure 51:
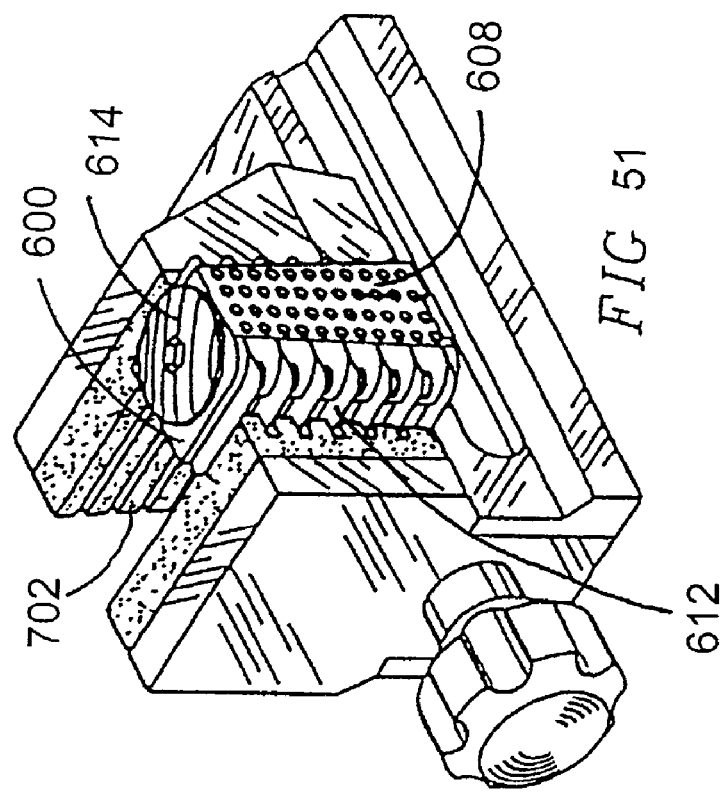
FIG. 51 is a side perspective view of the vise of FIG. 50 holding the implant of FIG. 49.
Figure 50:
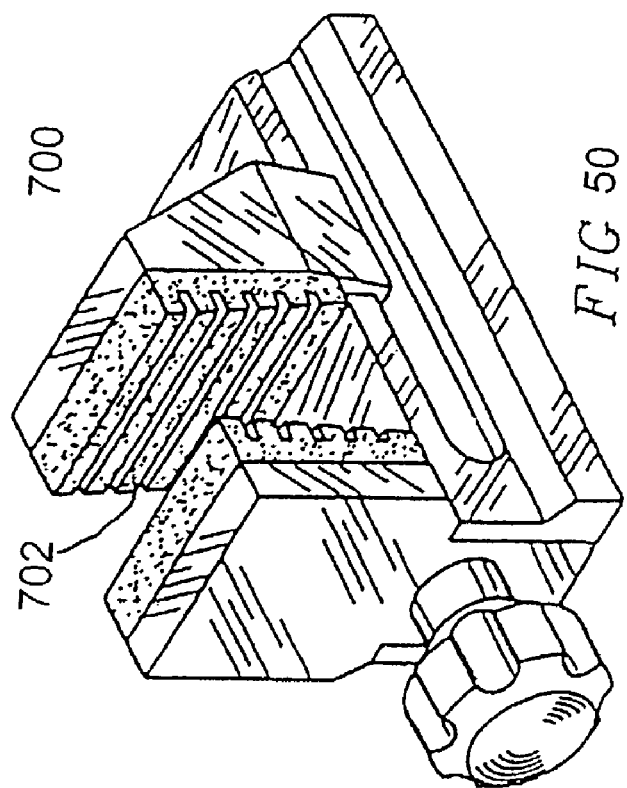
FIG. 50 is a side perspective view of a vise adapted to hold the implant of FIG. 49 for loading the implant with fusion promoting substances.

FIGS. 1-28 are generally directed to an embodiment of an instrument set having a rectangular cross-section for use in spinal surgery for forming a substantially quadrilateral space in the spine. FIGS. 34-41 are generally directed to another embodiment of the present invention surgical instrument set having a circular cross-section for forming a substantially quadrilateral space in the spine. FIGS. 29, 29A, 32, 33, and 42-48 generally show the space formed in the spine by the instrument sets of FIGS. 1-28 and 34-41 with implants for placement in the created space. FIGS. 49-51 generally show an implant and vise adapted to hold the implant for loading the implant with fusion promoting substances. An instrument set for use in spinal surgery is used to form a substantially quadrilateral space in the spine for implanting a spinal implant into a disc space between adjacent vertebral bodies.

The anterior aspect (front) of the spine may be exposed either by opening a surgical incision large enough to allow direct visualization or laproscopically with a small opening to allow instruments to be placed through the body from outside the body for visualization through an endoscope. The vertebral midline, which bisects the vertebral bodies along the longitudinal axis of the spinal column separating left from right is identified by the surgeon. As shown in FIGS. 1-4, an exemplary embodiment of a midline marker 100 of the present invention preferably is used to create reference marks at the vertebral midline on the disc material and on the adjacent vertebral bodies in a segment of the spine. Marker 100 has a shaft 102 terminating in an insertion tip 104 having a tapered leading edge 106 allowing it to be placed into a multitude of discs having various heights. Tapered leading edge 106 facilitates the insertion of marker 100 into the disc material contained in the disc space between two adjacent vertebral bodies. The juncture of shaft 102 and insertion tip 104 of marker 100 forms a shoulder 108 for butting against the anterior aspect of the adjacent vertebral bodies and thus prevents unwanted over penetration of insertion tip 104 into the disc space. Also located at shoulder 108 at the anterior aspect of shaft 102 are a plurality of dye exit holes 110. Dye exit holes 110 are in communication via a passage 112 with a syringe engaging well 114 located at a trailing end or proximal end 116 of shaft 102. Well 114 is adapted to receive the tip of a syringe (not shown), or any other well-known device for containing and injecting a dye into marker 100. A preferred marker 100 has advantages over a needle due at least in part to having a shoulder for preventing over penetration of the disc space or having the ability to provide multiple marks on the spine via multiple dye exit holes.

After marker 100 is inserted into the disc space, it may have its position confirmed radiographically to make sure that insertion tip 104 is accurately positioned at the vertebral midline and to assess the depth of the disc space relative to the known length of insertion tip 104. After marker 100 is correctly placed at the vertebral midline, a dye such as indigo carmine dye preferably is attached to marker 100 at well 114 at proximal end 116 of shaft 102. With injection, the dye flows through passage 112 within shaft 102 of marker 100 and exits dye exit holes 110 to create reference marks 118 at the vertebral midline on the adjacent vertebral bodies and on the disc material. The position of reference marks 118 corresponds to dye exit holes 110 at the leading end or distal end 120 of shaft 102 of marker 100. Marker 100 is then removed from the disc space and reference marks 118 remain on the vertebral bodies and disc material. Reference marks 118 are visible to the surgeon and are used as alignment reference points in guiding instruments into the spine.

Figure 1:
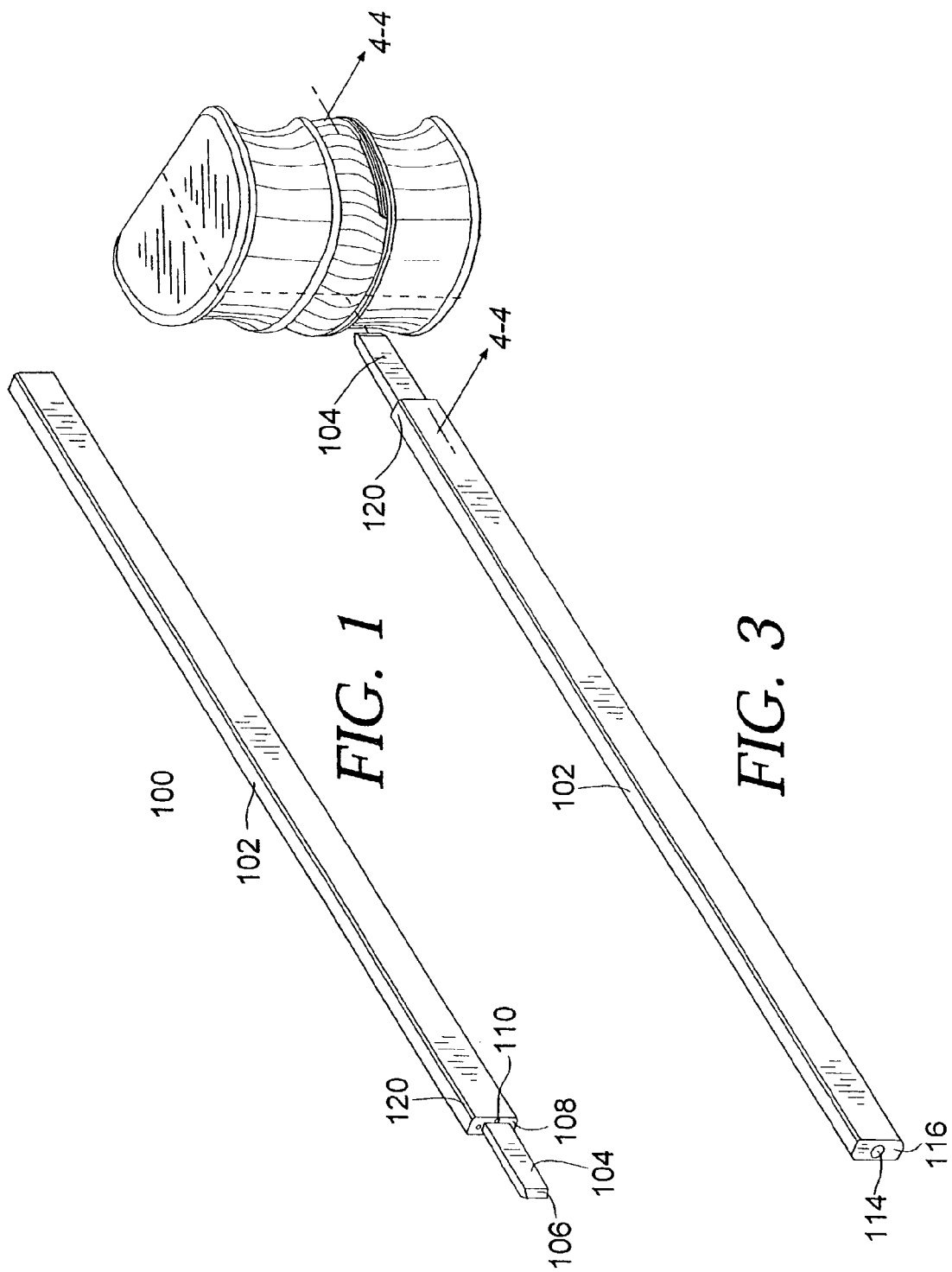
FIG. 1 is a leading end side perspective view of a midline spinal marker of the present invention.
Figure 2:
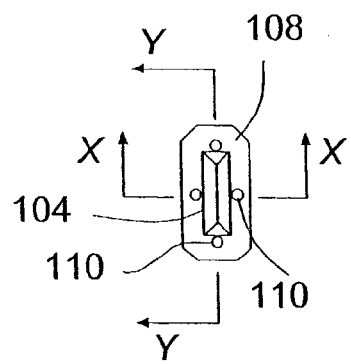
FIG. 2 is a leading end view of the midline spinal marker of FIG. 1.
Figure 2A:
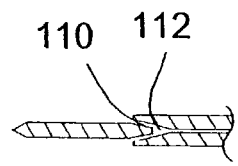
FIG. 2A is a cross-sectional view along lines X-X of FIG. 2.
Figure 2B:
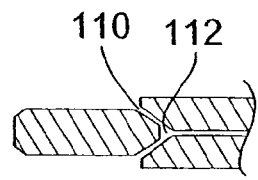
FIG. 2B is a cross-sectional view along lines Y-Y of FIG. 2.
Figure 4:
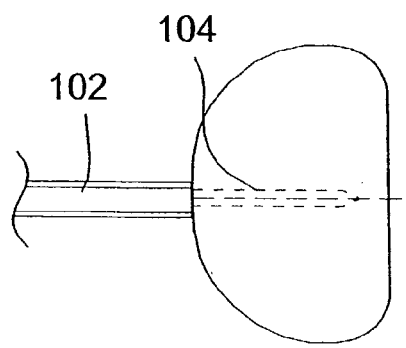
FIG. 4 is a cross-sectional view along lines 4-4 of FIG. 3 illustrating the spinal marker inserted into the disc space between two adjacent vertebral bodies along the vertebral midline.
Figure 5A:
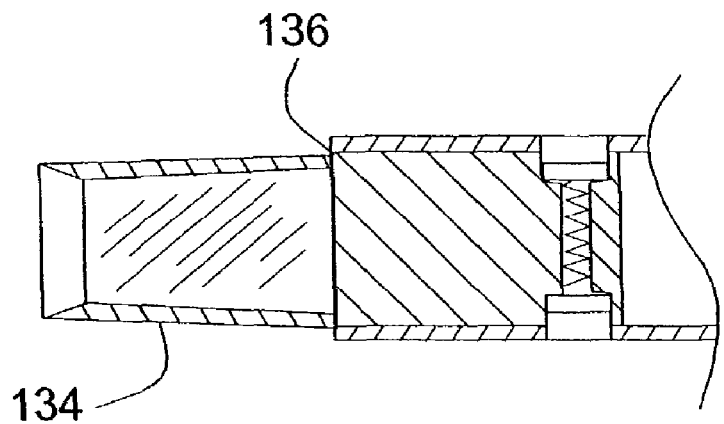
FIG. 5A is a cross-sectional view along line 5A-5A of FIG. 5.
Figure 7:
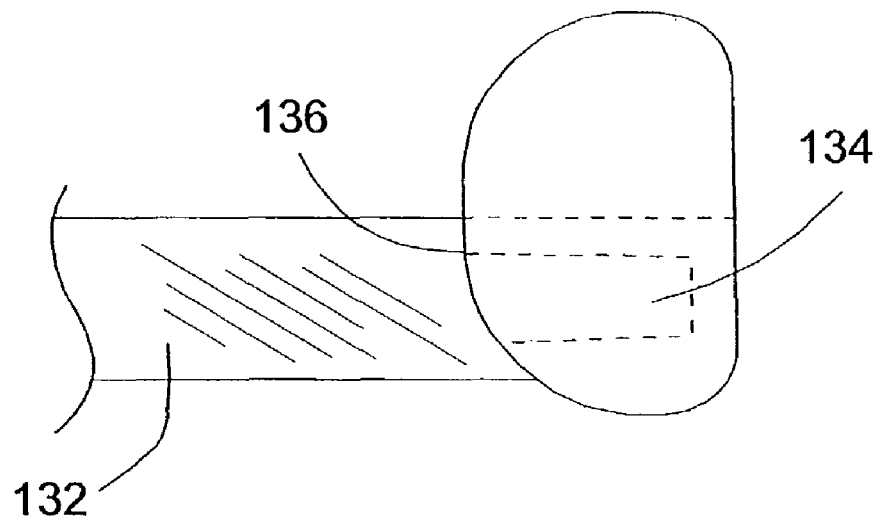
FIG. 7 is a cross-sectional view along line 7-7 of FIG. 6 showing the distractor inserted in the disc space between the adjacent vertebral bodies on one side of the vertebral midline.

As embodied herein, and as shown in FIGS. 5-7, an instrument set of the present invention may include a distractor 130 that urges two adjacent vertebral bodies apart and maintains the vertebral bodies in a selected spacial relationship to each other. Distractor 130 comprises a shaft 132 capable of receiving a graduated series of removable, partially hollow tips 134. The junction of shaft 132 and tip 134 forms a shoulder 136 that abuts against the two adjacent vertebral bodies when tip 134 is inserted between the two adjacent vertebral bodies. Shoulder 136 of shaft 132 preferably curves to correspond to the external curvature of the vertebral bodies adjacent the disc space in which distractor 130 is inserted. Tip 134 is preferably, but not requisitely, hollow to facilitate insertion into the disc material and to avoid displacing its own volume that might cause disc protrusion. Tip 134 has a height at its distal end of approximately 4-16 mm that increases to approximately 7-20 mm at the junction of tip 134 with shoulder 136 of shaft 132 to facilitate insertion of tip 134 into the disc space. When used anteriorly, tip 134 is generally of a lesser height at the leading end. A length of approximately 15-30 mm is preferred for use from anterior to posterior. The length of tip 134 is preferably 15-42 mm for use translaterally. The increase in height along tip 134 also may be used to position the two adjacent vertebral bodies in an angular spacial relationship, such as to create lordosis. Shaft 132 is preferably hollow to reduce the overall weight of distractor 130.

A proximal end 138 of distractor 130 comprises an extraction head 140 for coupling to an extraction instrument 150 described in detail below. While a preferred embodiment is shown, it is appreciated that a variety of configurations at proximal end 138 of distractor 130 could be utilized for the intended purpose, including but not limited to, threads, keyways that rotate and lock, male and female interlocking parts and the like without departing from the present teaching. Insertion of distractor 130 into the disc space preferably is guided by reference marks 118 created by marker 100. During insertion of distractor 130, shaft 132 of distractor 130 preferably is positioned to one side of the vertebral midline marked by reference marks 118.

Tip 134 of distractor 130 may be driven into the disc space by an impaction force imparted to distractor 130 through an impaction cap 160 which couples to proximal end 138 of distractor 130 and prevents damage to end 138 of distractor 130. In yet another alternative embodiment, an adapter engages distractor removing engagement means and the adaptor engages at its opposite end to a "T" handle that can be utilized with or without a mallet to install or remove distractor 130, or any of the other instruments that at their trailing ends are similarly configured. The depth of insertion of tip 134 of distractor 130 into the disc space is sufficient to achieve the desired distraction and vertebral alignment and is limited by shoulder 136 that abuts the two adjacent vertebral bodies to prevent any unwanted movement of tip 134 beyond the disc space.

As embodied herein, and as shown in FIGS. 8-11, an instrument set of the present invention may include a guard 170 having a hollow body 172 that terminates in an insertion end 174 that preferably curves to correspond to the external curvature of the two adjacent vertebral bodies of the spine. Extending from insertion end 174 of guard 170 are a pair of disc penetrating extensions 176 that are diametrically opposite one another on the sides of guard 170. Each of extensions 176 preferably have a wedged tip to facilitate insertion into the disc material between the two adjacent vertebral bodies. Extensions 176 have a height that preferably is less than the height of guard 170 such that a shoulder 178 is formed at the distal end 180 of guard 170 in which shoulder 178 functions as a depth limiting stop to prevent over penetration of extension 176 into the disc space.

Preferably, protruding from insertion end 174 of guard 170 also is a pair of prongs 182 for engaging the bone of the vertebral bodies. Prongs 182 function to engage guard 170 to the two adjacent vertebral bodies and to hold the two adjacent vertebral bodies in a selected spacial relationship. A proximal end 184 of guard 170 is open to permit insertion of instruments and implants into guard 170 as described in detail below. The internal opening of guard 170 is suitably dimensioned for receiving distractor 130. For laproscopic use, proximal end 184 of guard 170 can be attached to a laproscopic port allowing for the passage of instruments through the port and guard 170 while effecting a fluid and gas seal.

As embodied herein, and as shown in FIGS. 10 and 11, with distractor 130 inserted between the two adjacent vertebral bodies, guard 170 slidably engages proximal end 138 of distractor 130 and advances toward the spine with distractor 130 functioning as a guide post for aligning guard 170. Guard 170 seats into position with an impaction force imparted onto proximal end 184 of guard 170 via a large impaction cap 160. As shown in FIG. 12, impaction cap 160 has an internal configuration capable of receiving extraction head 140 of distractor 130 and has a shoulder portion 162 for abutting proximal end 184 of guard 170. Once extraction head 140 contacts the internal part of impaction cap 160, guard 170 can no longer advance and thus serves as a depth limiting stop. Guard 170, like distractor 130 and the bone compactor can also be installed and removed by use of the slap hammer, or an adaptor and mallet.

With particular reference to FIGS. 11, 12, and 12A, after guard 170 seats against and engages the spine, extensions 176 are positioned in the disc space at opposite sides of the insertion end of distractor 130. Extensions 176 serve to create or maintain a selected spacial relationship of the two adjacent vertebral bodies and also serve as guards to keep the surgical procedure within the area between extensions 176 and to prevent any unwanted movement of an instrument or implant outside of the area between extensions 176.

In an alternative embodiment of the present invention, guard 170 may be inserted directly into the spine without recourse to the preliminary use of distractor 130. In that case, it is preferred that the leading end of extensions 176 of guard 170 be configured so as to both facilitate the easy introduction of guard 170 into the disc space, and so as to urge the vertebral bodies apart into a distracted state. For this purpose, the most distal end of extensions 176 themselves would have a lesser height than the remainder of extensions 176 and preferably a pointed, tapered, radiused, or chamfered shape. It should be recognized that while the present instrument set provides means for identifying and achieving the optimal intervertebral distraction prior to the removal of any bone, it also provides for adjusting it later in the procedure via graduated spacer blocks and graduated guards having a variety of heights. While it is believed that the predistraction of the intervertebral space prior to bone removal is desirable, it is not requisite and it is anticipated that the present instrument set allows for the distraction of the intervertebral space later in the procedure, and/or by the insertion of the implant itself.

Figure 13:
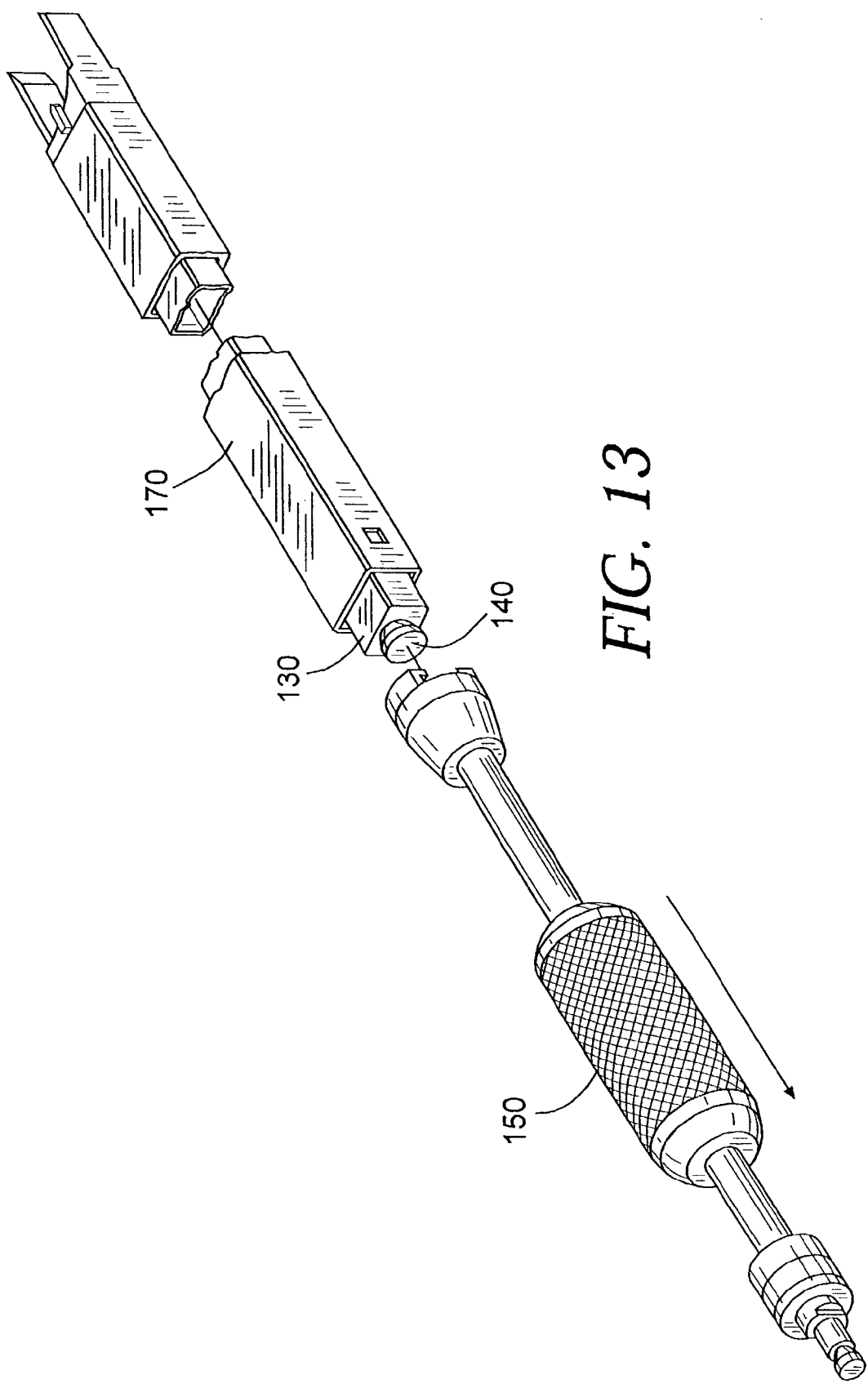
FIG. 13 is a trailing end side perspective view of an extraction instrument to remove the distractor from within the guard.
Figure 16:
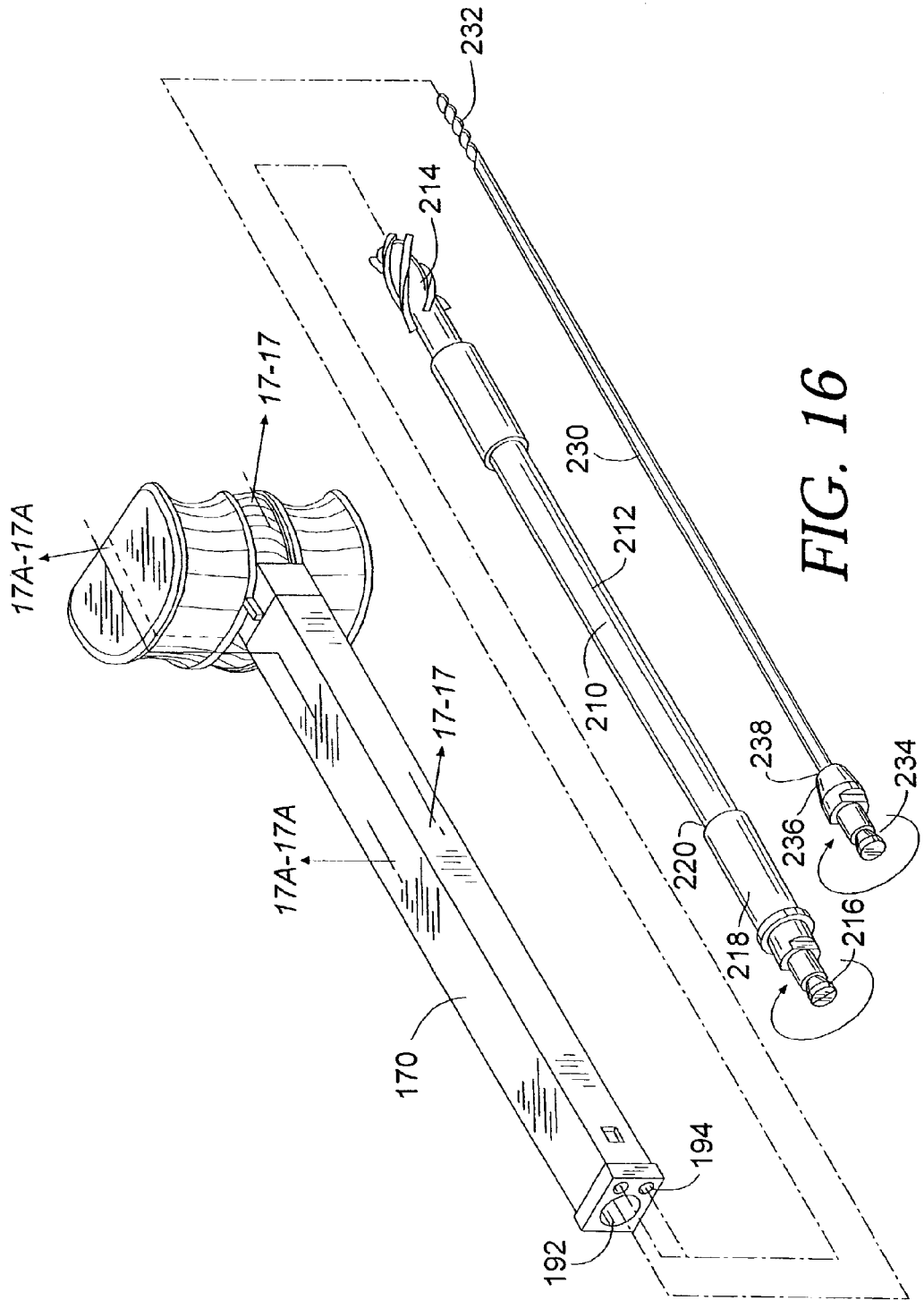
FIG. 16 is an exploded trailing end side perspective view of the guard with the guide and with a large drill bit and a small drill bit used to remove bone from the adjacent vertebral bodies.

As shown in FIG. 13, once guard 170 is seated, distractor 130 preferably is removed with an extraction instrument 150 which couples to extraction head 140 and may be advanced away from the spine with slap-hammer style advancement or pulled with a handle which couples to an end of extraction instrument 150.

As embodied herein, and as shown in FIGS. 14-18, an instrument set of the present invention may include a guide 190 for creating a quadrilateral space, or more particularly a rectangular space between the two adjacent vertebral bodies. Guide 190 preferably has a large bore 192 and two small bores 194 to one side of large bore 192. Guide 190 has a shaft 196 terminating in an insertion end 198 that is inserted into guard 170. Guide 190 also has a trailing end 200 that preferably has a dimension greater than the inside opening of guard 170 that functions as a depth limiting stop to prevent further insertion of guide 190 into guard 170.

Figure 17:
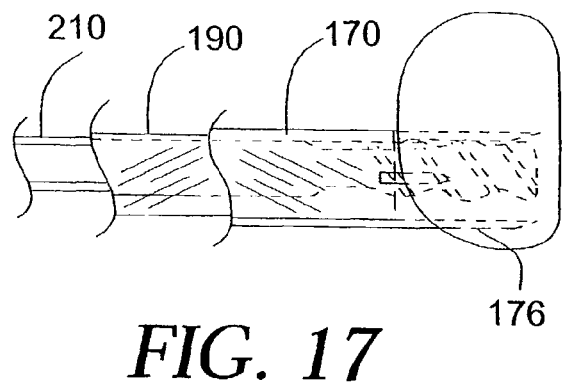
FIG. 17 is a cross-sectional view along lines 17-17 of FIG. 16 illustrating the guard, the large drill bit placed within the guide and extending into the disc space on one side of the vertebral midline.
Figure 17A:
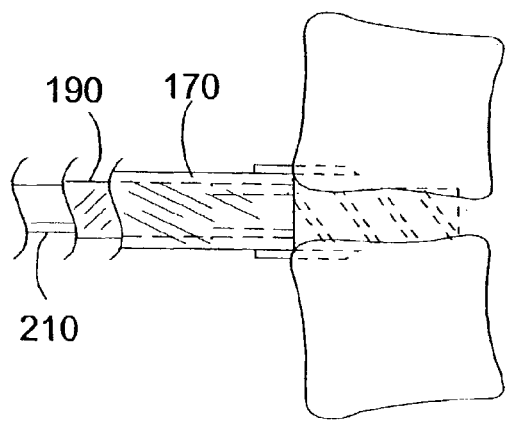
FIG. 17A is a cross-sectional view through the leading end of the drill assembly in the spine along lines 17A-17A of FIG. 16 illustrating the guard, the large drill bit placed within the guide and extending into the disc space on one side of the vertebral midline.

With particular reference to FIGS. 17 and 17A, a large drill bit 210 is shown having a longitudinal shaft 212 terminating at one end in a cutting portion 214 and having an engagement head 216 at the other end for engaging a rotating device, such as a handle or a power driven motor. A trailing end 218 of large drill bit 210 also includes a stop member 220 for abutting the surface of trailing end 200 of guide 190 to prevent unwanted over penetration of large drill bit 210 into the disc space. Large drill bit 210 is configured and dimensioned for placement through large bore 192 of guide 190.

Similarly, a small drill bit 230 terminates in a cutting end 232 and has an engagement head 234 for engaging a rotating handle or rotating motor. A trailing end 236 of small drill bit 230 also has an enlarged portion 238 for abutting the trailing end 200 of guide 190 to prevent unwanted over penetration of small drill bit 230 into the disc space.

In use, large drill bit 210 passes through large bore 192 in guide 190 to position the cutting portion 214 into the disc space and then is rotated to remove bone from the endplates of the two adjacent vertebral bodies. Large and small drill bits 210, 230 can be turned by a "T" handle or preferably by use of a power drill. Similarly, small drill bit 230 passes through small bores 194 of guide 190 to position cutting end 232 into the disc space and then rotates to remove bone from the endplates of the adjacent vertebral bodies. As shown in FIG. 17, extensions 176 of guard 170 protect the unwanted movement of large and small drill bits 210, 230 in a lateral or transverse direction and confine the drilling products so that they are evacuated by drill bits 210, 230.

Figure 18:
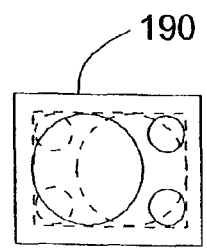
FIG. 18 is a diagrammatic representation of the hole pattern formed with the guide and large and small drill bits of the present invention after a first drilling, then rotating the guide 180° and performing a second drilling.

As shown in FIG. 18, the holes created with large drill bit 210 and small drill bit 230 form a pattern as indicated in solid lines in the drawing.

After the first three holes have been drilled, guide 190 is removed from within guard 170. Guide 190 then is rotated 180 degrees and reinserted into guard 170. Guide 190 now is oriented such that large bore 192 is positioned over the area in which the small holes were previously drilled and small bores 194 are positioned over the area in which the large bore was previously drilled. The drilling procedure with large drill bit 210 and small drill bit 230 is repeated to create a pattern of holes as indicated by the dotted lines in FIG. 18. The result of this drilling procedure, is the removal of a portion of bone from the endplates of the adjacent vertebral bodies creating a space approximating the configuration of a rectangle.

Although the drilling of the bone of the endplates creates a space with a configuration that approximates the shape of a rectangle, if desired a perfect rectangle may be obtained by use of a rectangular bone compactor.

As shown in FIGS. 19-21, a box-shaped bone compactor 240 has a shaft 242 terminating in a compaction end 244. Compaction end 244 of shaft 242 may include beveled, radiused, or thinned edges to ease introduction. Compactor end 244 compresses any remaining boney protuberances into the vertebral bodies achieving a perfectly rectangular space. A trailing end 246 of shaft 242 may include an extraction head 248 for coupling to an extraction instrument 150.

In a preferred embodiment, there is no fixed stop until approximately 32-36 mm, so that a slotted and calibrated impaction cap 260 can be used to predictably and adjustably insert compaction end 244 into the intervertebral space to the desired optimal depth. Alternatively, compactor 240 can have a fixed depth limiting means. As a further alternative, leading edges 250 of compactor 240 can be sharpened so that it functions wholly or in part as a chisel to cut rather than compact the bone. This is considered less desirable, though still workable, than the preferred compaction end 244 by which the density of the bone at the prepared recipient site is actually increased by the compaction process.

Compactor 240 is inserted into guard 170 and advanced by an impaction force imparted to the trailing end 246 of compactor 240 by an impaction cap 260 similar to the impaction cap previously described above. The advancement of compaction end 244 of compactor 240 impacts the remaining portions of the bone that were not removed in the drilling step previously described into the vertebral bodies themselves.

As an alternative to compactor 240, trial size spacers 291 resembling implants 290 with either smooth or abrading surfaces may be impacted into the space to complete the flattening of the opposed bone surfaces.

As show in FIGS. 22A-C, a handle assembly 270 is shown for coupling to the drilling instrumentation and other instruments of the present invention. Compactor 240 is removed from within guard 170 by coupling to extraction instrument 150 and advanced outside of guard 170 with extraction instrument 150 shown in FIGS. 13 and 26.

Figure 23:
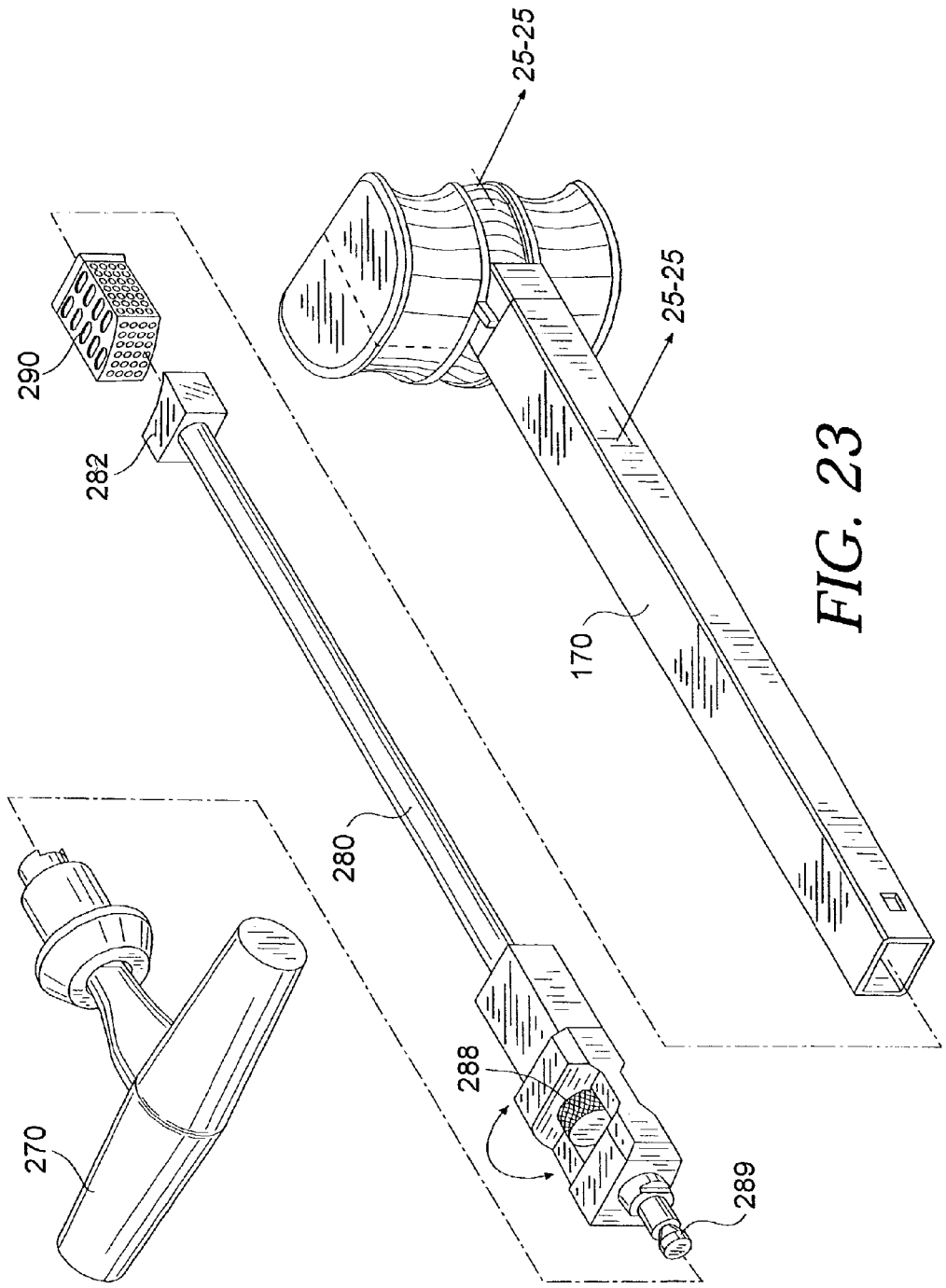
FIG. 23 is an exploded trailing end side perspective view of the guard in place with a handle for an implant driver and an implant for implanting through the guard and into the space between the two adjacent vertebral bodies created by the instrumentation and method of the present invention.
Figure 24:
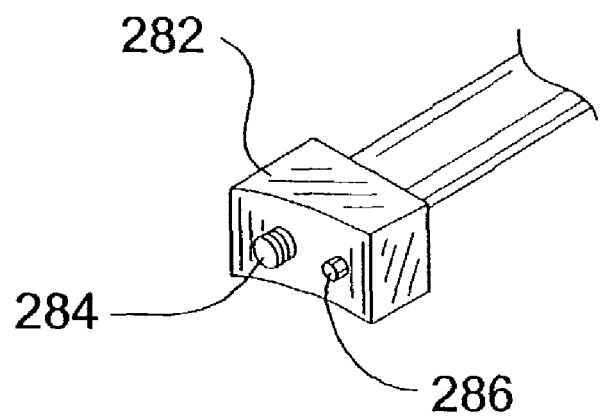
FIG. 24 is a fragmentary leading end view of the implant driver instrument of FIG. 23.
Figure 25:
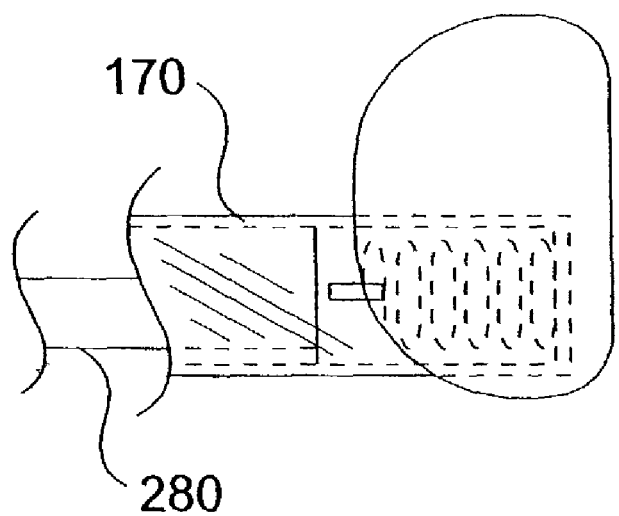
FIG. 25 is a cross-sectional view along lines 25-25 of FIG. 23 illustrating the implant driver instrument and implant inserted through the guard and into the space created between the two adjacent vertebral bodies on one side of the vertebral midline.

FIGS. 23-25 show a driver 280 for inserting an intervertebral implant 290 into the created space between the two adjacent vertebral bodies. Driver 280 has a leading end 282 configured to cooperatively engage an implant 290. As shown in FIG. 24, driver 280 has a threaded portion 284 and a non-threaded pin 286 extending from the leading end 282 for insertion into corresponding openings in the trailing end of the implant 290. Threaded portion 284 is rotatable by a knob 288 at the opposite end of driver 280 so as to threadably couple driver 280 to implant 290. Driver 280 has a handle coupling means 289 for coupling to handle assembly 270 for controlling driver 280.

After implant 290 is coupled to driver 280, implant 290 and leading end 282 of driver 280 are inserted into guard 170 and advanced towards and into the created space between the two adjacent vertebral bodies. After implant 290 has been placed within the created space by use of the "T" handle with or without impaction of the slap hammer, or an adaptor and a mallet, knob 288 of driver 280 is rotated to uncouple implant 290 from driver 280. Driver 280 then is removed from within guard 170 leaving implant 290 inserted in the created space.

It is clearly anticipated that while the specific configuration of the preferred ends has been described, that a variety of threaded and non-threaded means for coupling implants 290 to driver 280 could in the alternative be employed without departing from the present inventive concept.

Figure 26:
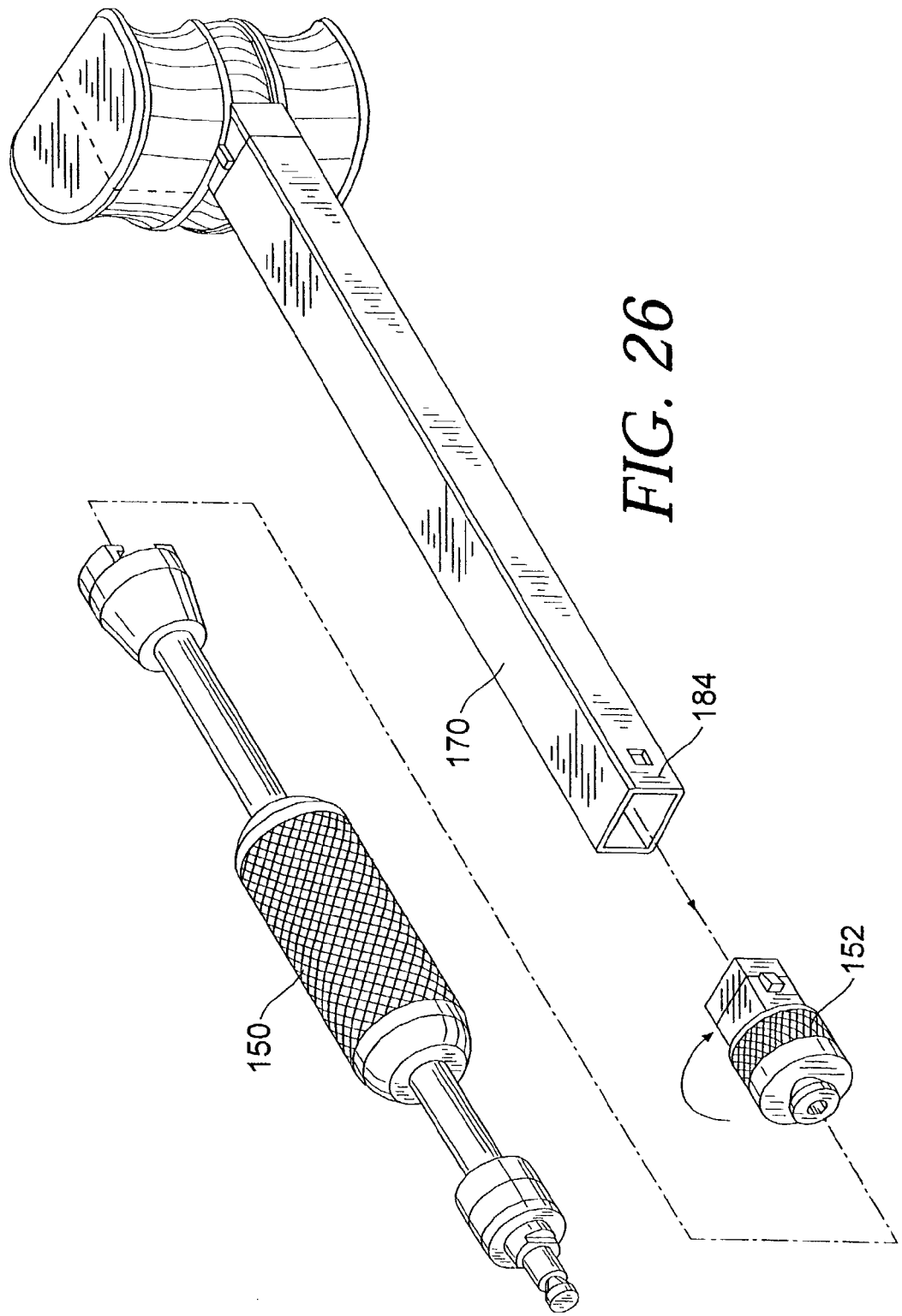
FIG. 26 is an exploded side perspective view of the guard, an extraction adapter for engaging the guard and, and an extraction instrument for engaging the adapter and for extracting the guard.

FIG. 26 shows guard 170 being removed from the disc space and from the adjacent vertebral bodies with extraction assembly 150 which couples to an extraction adapter 152 configured to fit within the proximal end 184 of guard 170. Extraction adapter 152 is locked into place by a spring-biased butterfly member that fits into corresponding notches at the proximal end 184 of guard 170. After extraction assembly 150 is coupled to guard 170, extraction assembly 150 is advanced away from the spine with a slap-hammer style motion or any other suitable means to remove guard 170 from the spine. After guard 170 is removed, implant 290 remains in place in the created space between the endplates of the two adjacent vertebral bodies.

FIGS. 27 and 28 show that the procedure being repeated on the opposite side of the vertebral midline. Distractor 130 and guard 170 are rotated 180 degrees to conform to the curvature of the vertebral bodies on the second side of the vertebral midline. The above steps for the present invention are repeated for inserting guard 170 into position on the opposite side of the vertebral midline. As shown in FIG. 28, first implant 290 is positioned and remains within the created space between the adjacent vertebral bodies and guard 170 is positioned on the opposite side of the vertebral midline to first implant 290.

Figure 29:
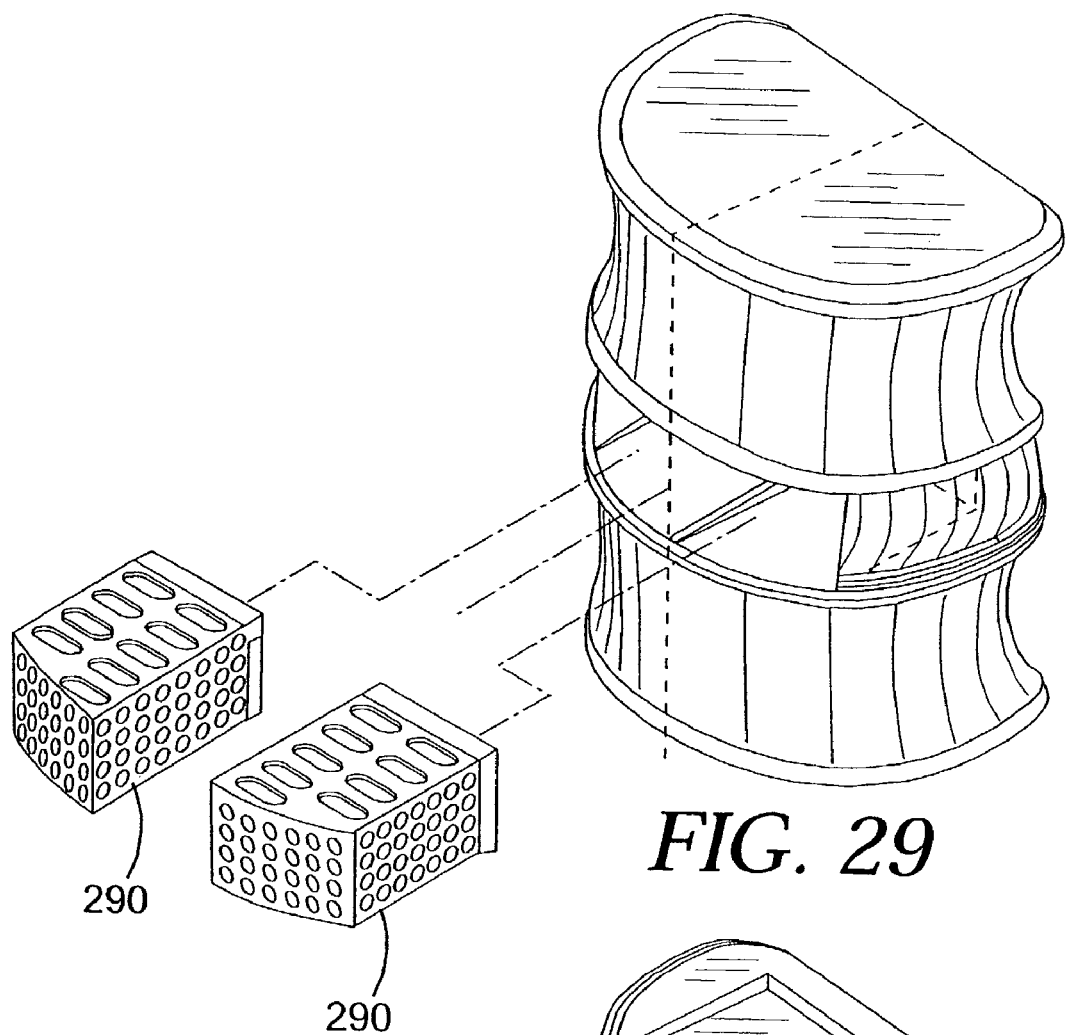
FIG. 29 is an exploded side perspective view of a segment of the spine prepared to receive two implants with the instrumentation and method of the present invention.
Figure 29A:
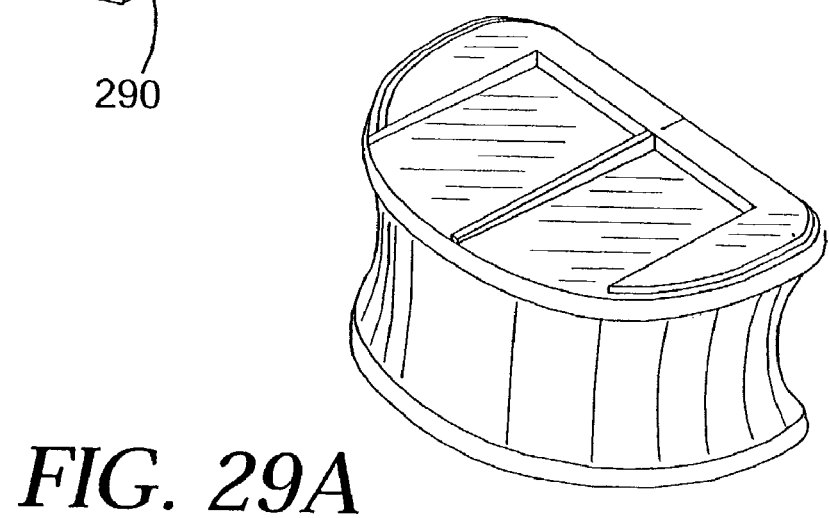
FIG. 29A is a top perspective view of the lower vertebral body of the segment of the spine of FIG. 29.
Figure 30:
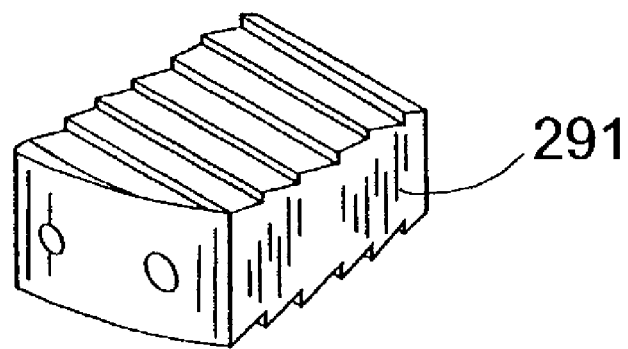
FIG. 30 is a trailing end perspective view of a spacer of the present invention.
Figure 31:
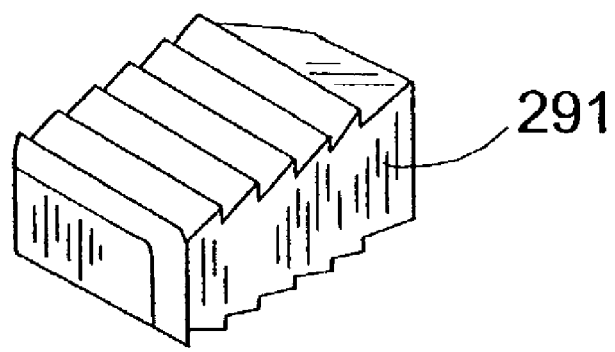
FIG. 31 is a leading end perspective view of a spacer of the present invention.

As shown with implant 290 in FIG. 29 and a spacer block 291 in FIG. 31, either of implant 290 or spacer block 291 may be inserted in the space created in the spine. As shown in FIGS. 30 and 31, spacer block 291 may have an external configuration similar to that of the implant, except that it may be more or less solid. It is appreciated that spacer blocks 291 and implants 290 may be wedged-shaped or rectangular so as to adjust the angular relationship of the vertebral bodies to each other.

Figure 32:
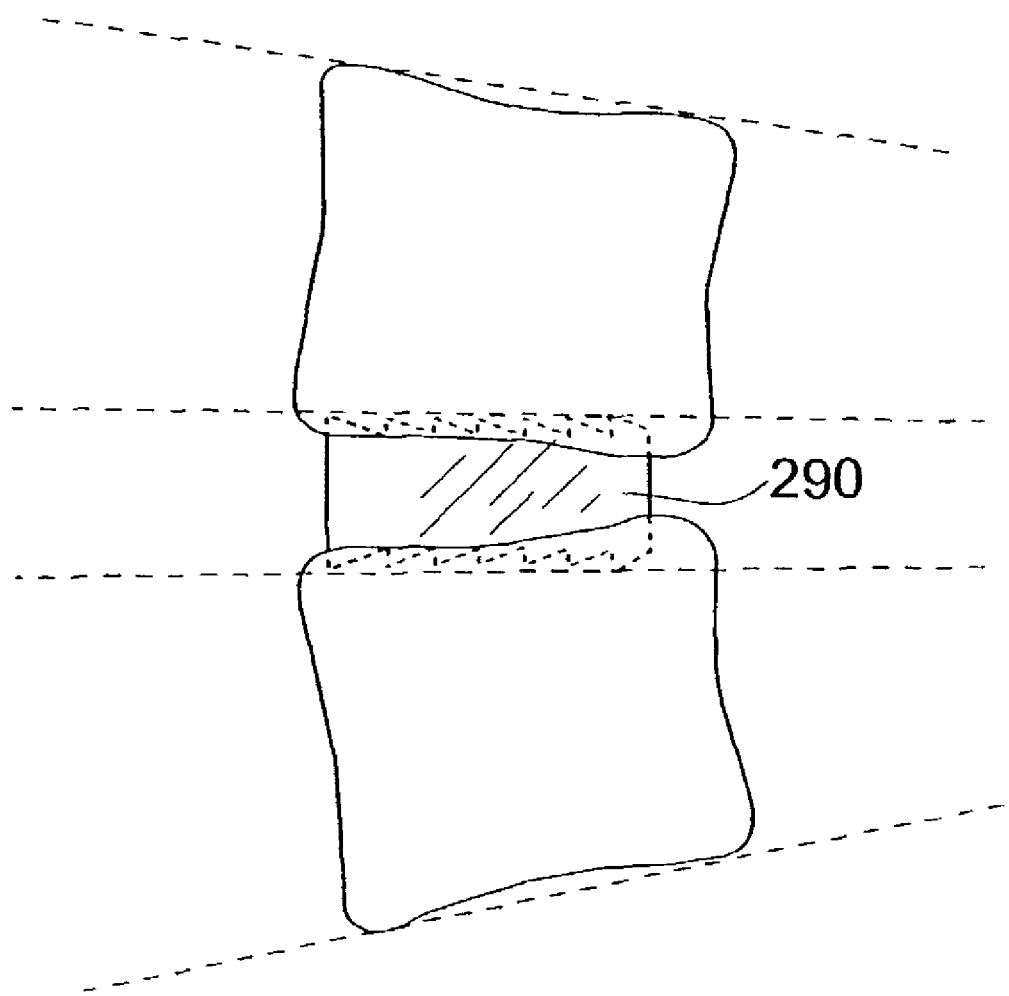
FIG. 32 is a side elevational view of two adjacent vertebral bodies in lordosis with an implant inserted into a space created between two adjacent vertebral bodies in which the created space has a lordotic configuration with an implant having parallel upper and lower surfaces maintaining the angular relationship of the adjacent vertebral bodies.
Figure 33:
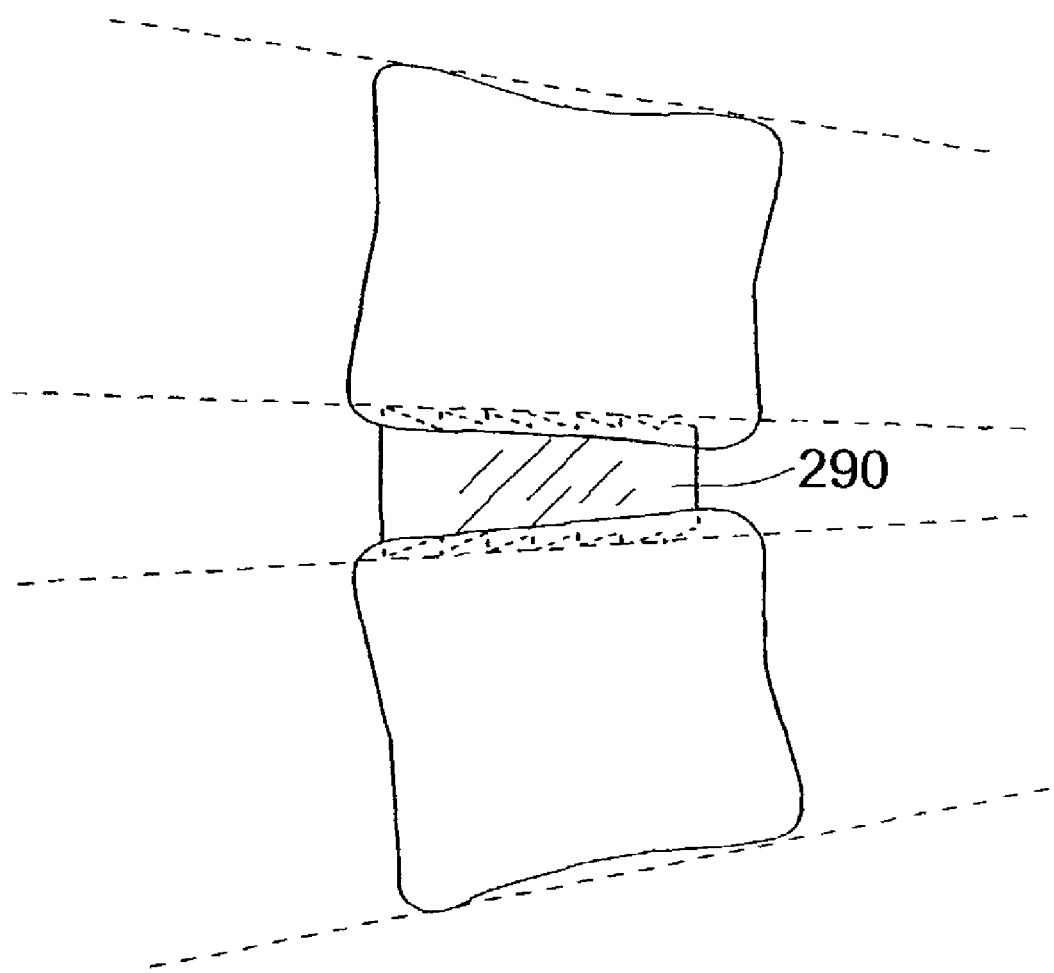
FIG. 33 is a side elevational view of two adjacent vertebral bodies in lordosis with a lordotic implant placed between the two adjacent vertebral bodies in a space created between the two adjacent vertebral bodies.

As shown in FIGS. 32 and 33, the instrumentation and method of the present invention may be used to create or maintain lordosis of the spine in at least two ways and to accept both generally rectangular and trapezoidal implants. As shown in FIG. 32, the created space may be formed at an angle to the vertebral endplates, such that the planes of the top and bottom surface of the created space are in an angular relationship to each other. The two adjacent vertebral bodies are positioned in angular relationship to each other with the insertion of implant 290 having parallel upper and lower surfaces within the created space. The insertion of implant 290 into the angular space causes the vertebral bodies to be placed in an angular relationship.

FIGS. 32 and 33 show two adjacent vertebral bodies in a desired lordotic angular relationship. In FIG. 32, the space was created by means of the shape of extensions 176 on guard 170 during the drilling and compaction procedure. A rectangular space was formed with more bone removed posteriorly than anteriorly in anticipation of receiving a generally rectangular implant 290. This is a preferred stable configuration as the compressive loads of the spine onto implant 290 are received generally perpendicular to the surface (rather than on an angle that might urge the implant forward or backwards). Additionally, once installed implant 290 is blocked from further penetration by the wall of bone created by the removal of the bone before it, and is blocked from backing out because the implant upper and lower surfaces would need to move against the inclined slanted surfaces of the vertebral bodies in order to move and that would require significantly more energy than remaining in the more stable position of being fully installed.

For the space shown in FIG. 33, extensions 176 of guard 170 were positioned between the vertebral bodies so that the adjacent vertebral surfaces were generally parallel during the creation of the recipient space. This was done in anticipation that the desirable lordosis would be achieved by the use of an implant at least in part generally trapezoidal in shape, or having upper and lower surfaces for engaging the adjacent vertebral bodies, which surfaces are in a non-parallel angular relationship to each other.

While this is theoretically a less stable configuration than that previously described, it offers the advantage that the amount of bone removal is minimal but sufficient for its intended purpose and the thickness of the bone removed is more uniform in thickness.

As shown in FIG. 33 instead of creating an angular space, the created space may have parallel upper and lower surfaces. The two adjacent vertebral bodies are positioned in an angular relationship to each other with the insertion of an implant having upper and lower surfaces that are angled toward each other.

FIGS. 34-41 show a second set of instrumentation similar to the first in that it provides both for the creation of a generally rectangular or trapezoidal space in a non-traumatic way and for the insertion of an implant through the same instrumentation, but differs in that the guard is generally cylindrical while the prior guard was generally rectangular. A rectangular shape has less volume and space than a cylindrical shape, which has no corners and is less expensive to manufacture.

FIGS. 34-36 show a second embodiment of a guard of the present invention. Guard 370 has a hollow body 372 that terminates in an insertion end 374, which is removably coupled to body 372. The distal end 380 of guard 370 is curved to correspond to the external curvature of the two adjacent vertebral bodies the spine. Extending from the insertion end 374 are a pair of extensions 376 in a diametrically opposite position on the sides of the insertion end 374. Each of the two extensions 376 have a suitable configuration to facilitate insertion into the disc material between the two adjacent vertebral bodies. As shown in FIG. 35, extensions 376 may have an "anatomic" configuration to conform to the contours of the vertebral endplates adjacent to the disc space in which guard 370 is to be inserted. Preferably, but not requisite, also protruding from the insertion end 374 are a pair of prongs 382 for engaging the bone of the adjacent vertebral bodies. Prongs 382 function cooperatively with extensions 376 to engage guard 370 to the adjacent vertebral bodies and to hold the two adjacent vertebral bodies in a selected spacial relationship. The proximate portion of insertion end 374 may include a threaded portion for threadably coupling to body 372 of guard 370. It is appreciated that other coupling means are anticipated without departing from the scope of the present invention.

Figure 35A:
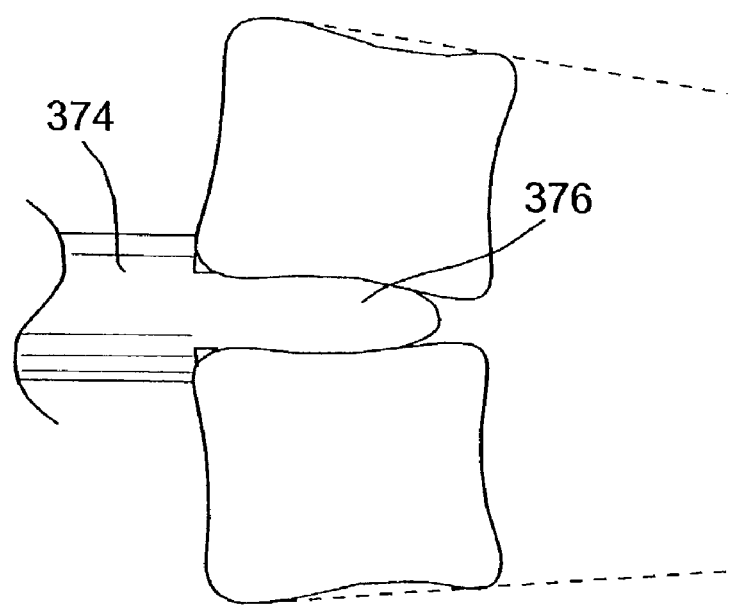
FIG. 35A is a side elevational view of an alternative embodiment of a removable insertion end.
Figure 35B:
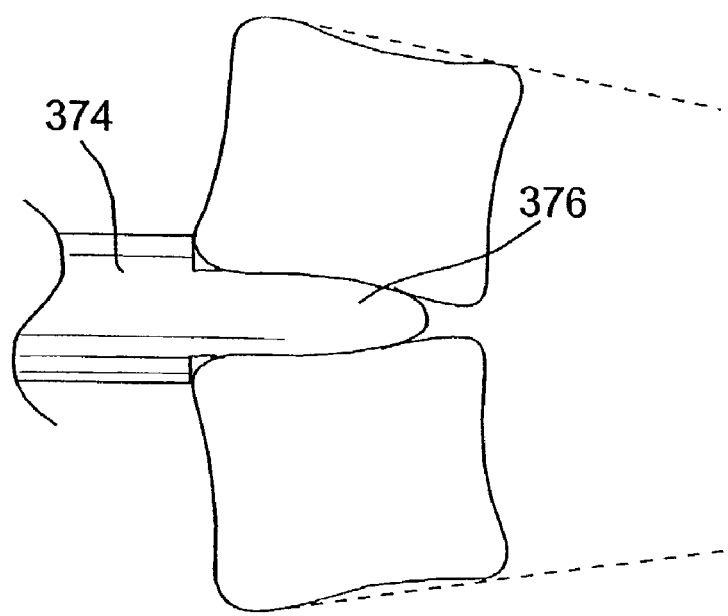
FIG. 35B is a side elevational view of yet another alternative embodiment of a removable insertion end.

FIG. 36 shows body 372 having a collar 404 which has a thread to engage the threaded portion of the removable insertion end 374. Guard 370 provides the added advantage of having interchangeable removable insertion ends 374 with different shaped extensions depending on the surgical procedure being employed. For example, instead of having an anatomical configuration, the extensions may have a parallel configuration as shown in FIG. 35A or may have a wedged configuration as shown in FIG. 35B, so as to allow the surgeon to achieve the desired angular relationship of the vertebral bodies to be fused.

Proximal end 384 of hollow guard 370 is open to permit the insertion of other instruments and implants into the guard as described herein. As with the previously described guard, a closeable part may be connected to the proximal end 384 of this guard for laproscopic use allowing for the passing of instruments through guard 370 while providing for a gas and fluid seal.

Guard 370 is seated into the disc space and engaged to the spine by being manually advanced or by imparting an impaction force onto the proximal end 384 of guard 370. As shown in FIG. 34, an insertion and extraction handle assembly 270 is shown with a coupling member for engagement to proximal end 384 of guard 370.

As shown in FIG. 38, after guard 370 is properly seated and engaged to the spine, extensions 376 are positioned in the disc space between the two adjacent vertebral bodies on one side of the vertebral midline. Extensions 376 serve to maintain the spacial relationship of the two adjacent vertebral bodies and also serve as guards to maintain an instrument or implant within the area between extensions 376 and to prevent any unwanted movement of an instrument or implant outside of the area between extensions 376.

FIG. 37 shows a guide 390 for creating a rectangular space between the two adjacent vertebral bodies. Guide 390 comprises a large bore 392 and two small bores 394 to one side of large bore 392. Guide 390 has a shaft 396 terminating in an insertion end 398 that is capable of being inserted into guard 370 and has a trailing end 400 having a dimension greater than the inside opening of guard 370 so as to act as a depth limiting stop to prevent further insertion of 390 guide into guard 370. Moreover, guide 390 is prevented from rotating within guard 370 by pins 402, which fit into the corresponding grooves at the proximal end 384 of the guard 370.

Figure 39:
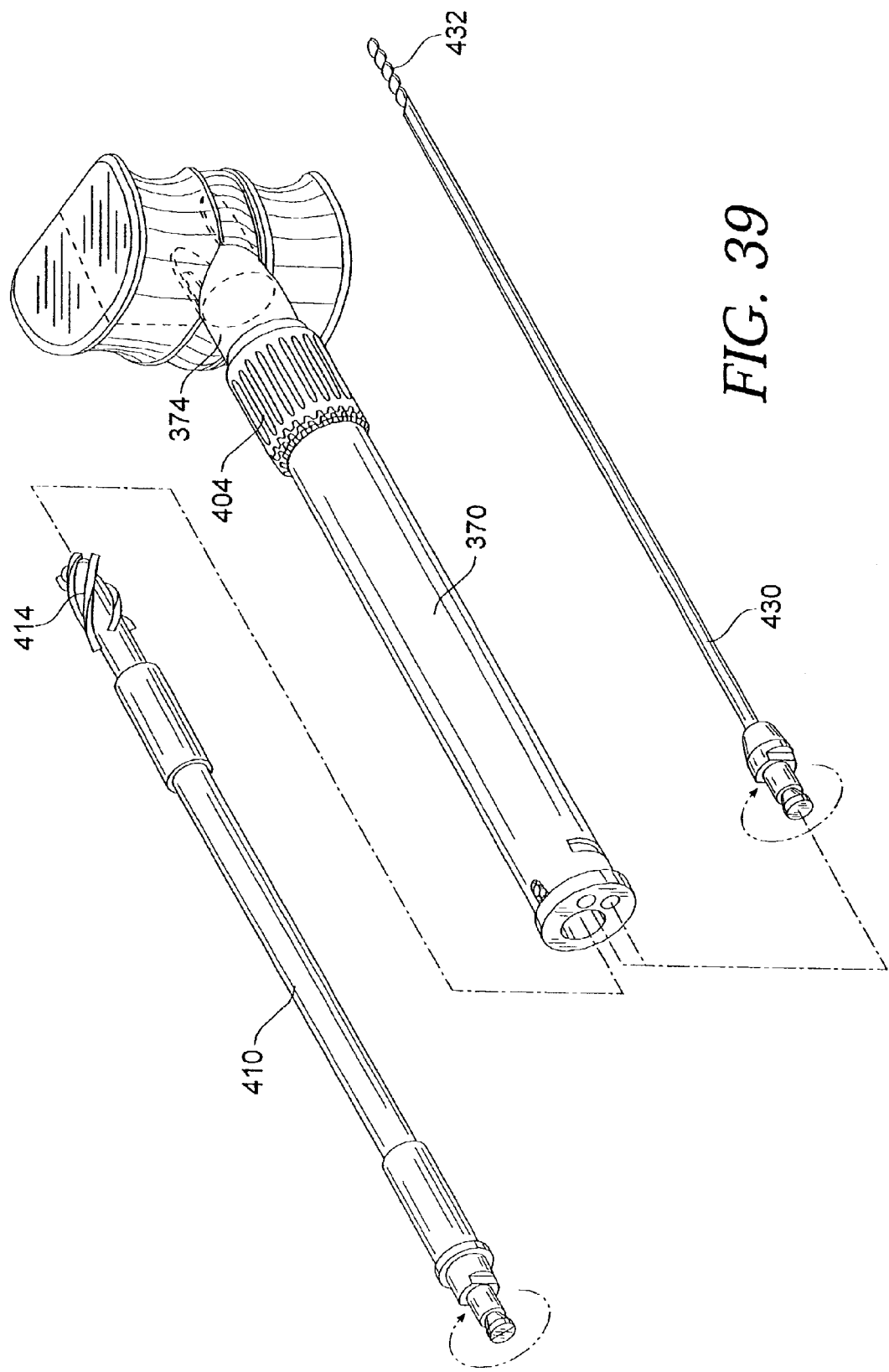
FIG. 39 is a trailing end side perspective view of the guard with the drill guide inserted into the guard and with a large drill bit and a small drill bit of the present invention used to remove bone from the adjacent vertebral bodies.

FIG. 39 shows a large drill bit 410 and a small drill bit 430 configured similarly to large and small drill bits 210, 230 described above with specific reference to FIG. 16. In use large drill bit 410 is passed through large bore 392 in guide 390 to position cutting end 414 into the disc space and is then rotated to remove bone from the endplates of the two adjacent vertebral bodies. Similarly, small drill bit 430 is passed through the small bores 394 of guide 390 to position cutting end 432 into the disc space and then rotated to remove bone from the endplates of the adjacent vertebral bodies.

Figure 42:
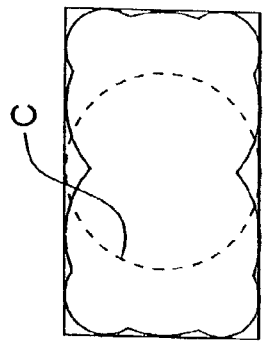
FIG. 42 is a diagrammatic illustration of the hole pattern formed with the guide and the large and small drill bits of the present invention.
Figure 43:
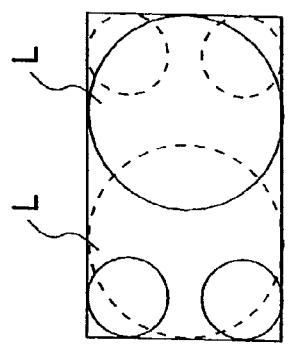
FIG. 43 is a diagrammatic illustration of the hole pattern formed after the drill guide instrument is flipped 180 degrees and additional holes are drilled with the large and small drill bits of the present invention.

As shown in FIG. 42, the holes created with large drill bit 410 and small drill bit 430 form a pattern as indicated in the dotted lines. After the first three holes have been drilled to provide a large hole L and two small holes S, guide 390 is removed from within guard 370 and guide 390 is rotated a 180 degrees and reinserted into guard 370. Guide 390 is now oriented such that large bore 392 is positioned over the area in which the small holes S were drilled and small bores 394 are positioned over the area in which the large hole L was drilled. The drilling procedure with large drill bit 410 and small drill bit 430 is repeated to create a pattern of holes as indicated by the dotted lines in FIG. 43. As a result of this drilling procedure, a substantial portion of bone is removed from the endplates of the adjacent vertebral bodies creating a space approximating the configuration of a rectangle.

Figure 40:
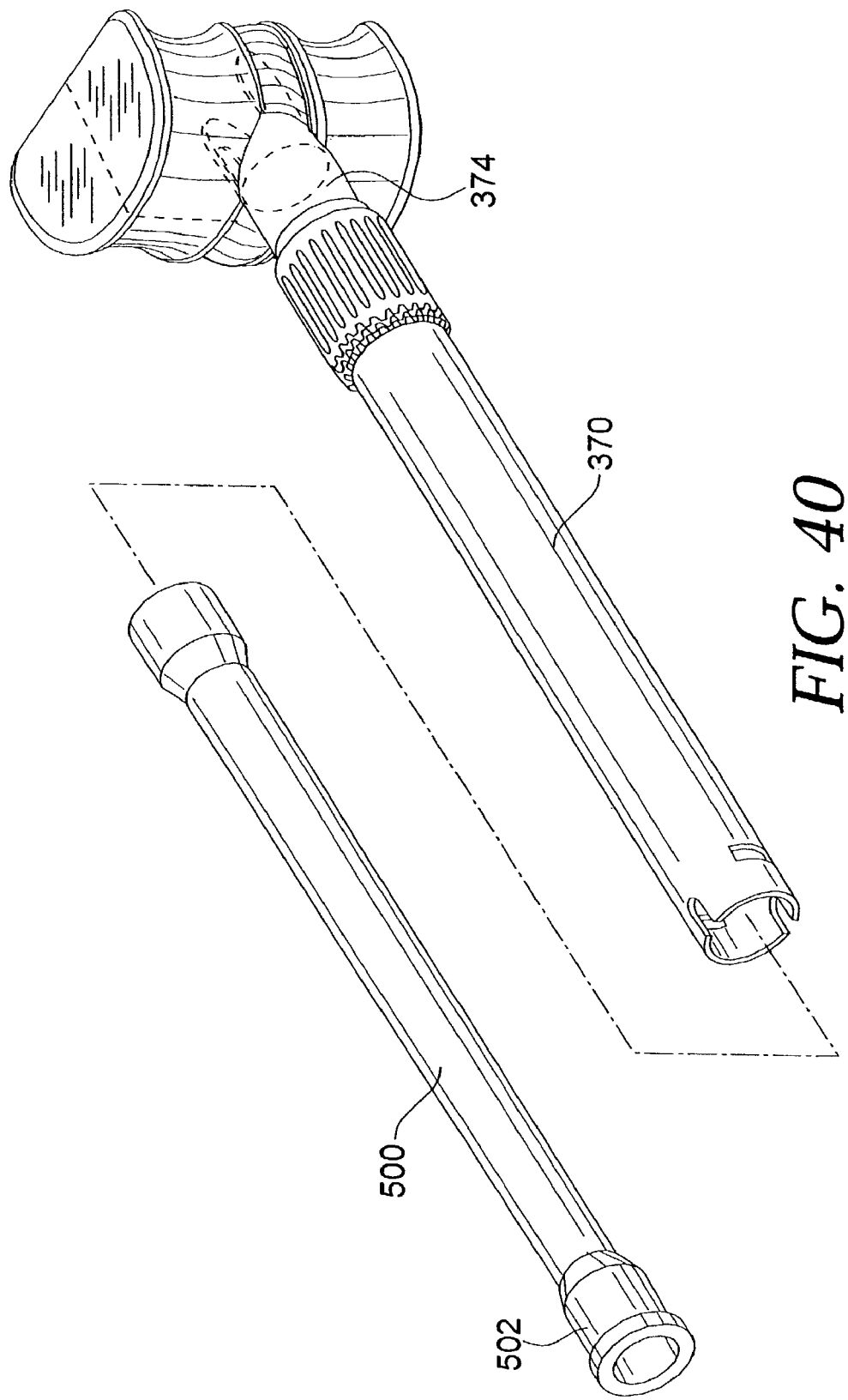
FIG. 40 is a trailing end side perspective view of the guard inserted on one side of the vertebral midline and into the disc space between two adjacent vertebral bodies and a central bore guide of the present invention for insertion therein.
Figure 41:
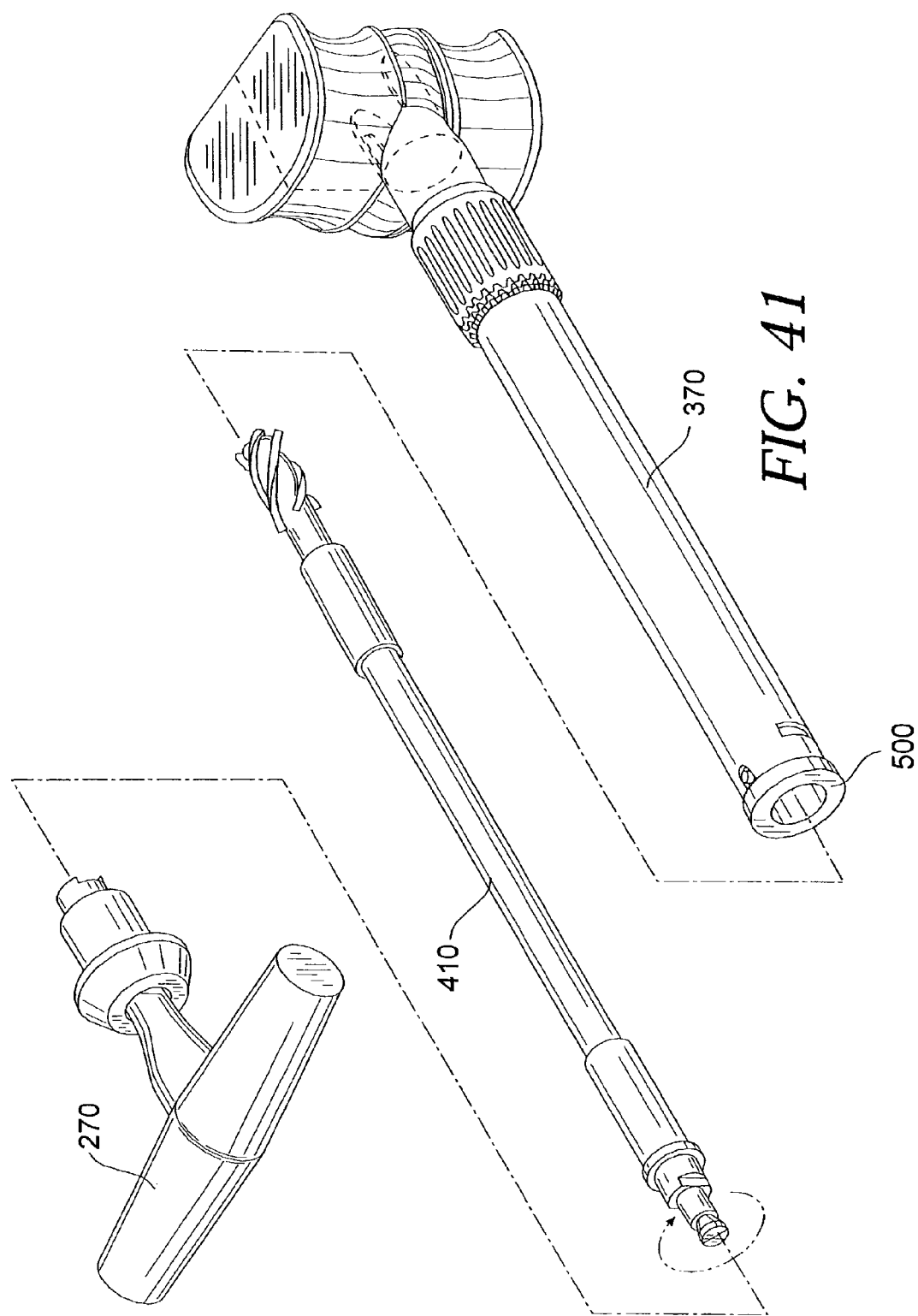
FIG. 41 is a trailing end side perspective view of the central bore guide inserted in the guard and the large drill and a handle assembly of the present invention.
Figure 44:
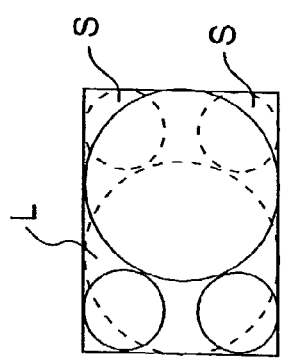
FIG. 44 is a diagrammatic illustration of the space created with the drill guide method of FIG. 43, but where the space to be prepared is wider than in FIG. 43.
Figure 45:
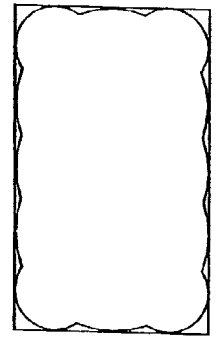
FIG. 45 is the configuration of the space created with the drill guide instrument and the holes drilled as shown in FIG. 44.
Figure 46:
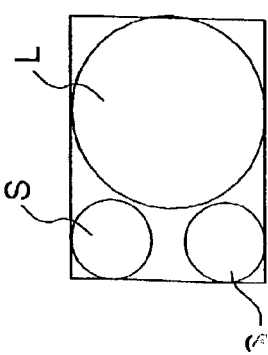
FIG. 46 is a diagrammatic illustration of a hole drilled with a central bore drill guide into the space of FIG. 45 of the present invention.

As shown in FIG. 40, as the central portion of the space created may not have all of the bone removed from the drilling procedure through guide 390, a central bore guide 500 may be inserted into guard 370. Central bore guide 500 has a large bore 502 that is centrally placed, such that when large drill bit 410 is passed through central bore guide 500, the portion of bone remaining in the central portion of the space being created can be removed. As shown in FIG. 44, the use of central bore guide 500 may be of particular value in removing remaining bone where guide 390 has a hole pattern that when reversed provides for a lesser amount of overlap of bores formed through large bore 392. FIG. 45 shows the space created with the drilling procedure through FIG. 44. Central hole C created with central bore guide 500 is shown in dotted line in FIG. 46.

Figure 47:
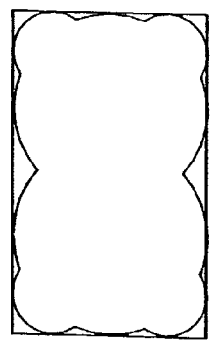
FIG. 47 is the configuration of the space created with the drill guide instrument and central bore drill guide instrument of FIG. 46 of the present invention.

As shown in FIG. 47, the space created with the drilling procedure with the present invention results in a substantial portion of bone being removed from the endplates of the adjacent vertebral bodies creating a space that more closely approximates the configuration of a rectangle.

Figure 48:
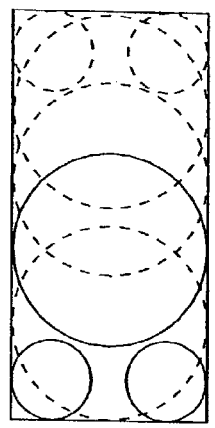
FIG. 48 is another diagrammatic illustration of a space created with multiple holes drilled with a central bore drill guide in accordance with the present invention to prepare a still wider space.

FIG. 48 shows a space created with the drilling procedure of the present invention to prepare a still wider space with a template pattern for the guide having a hole pattern that uses an offset central drill guide to drill two additional large bores to remove additional bone to form the space.

By way of example only, impacted implant 290 has been illustrated as one type of implant that could be inserted into the opening formed in the spine by the various embodiments of instrumentation and methods of the present invention. By way of another example, without limitation to use of any other type of implant, a self-broaching, rotatable impacted implant such as disclosed in U.S. application Ser. No. 09/429,628, which is hereby incorporated by reference herein, could also be inserted into the opening formed in the spine by the instrumentation and methods disclosed herein.

With reference to FIG. 49, an interbody spinal fusion implant is indicated generally as 600. The implant has a body 602 having an insertion end 604, a trailing end 606, opposed side walls 608, and opposed upper and lower walls 610. Body 602 has a cross section with side walls 608 intersecting the upper and lower walls 610 at junctions that are preferably two diametrically opposed corners and two diametrically opposed arcs. Fin-like projections 612 extend outwardly from respective ones of upper and lower walls 610 and are adapted to penetrate the vertebral endplates of the adjacent vertebral bodies upon rotation of implant 600 while the upper and lower walls 610 support the vertebral endplates of those adjacent vertebral bodies. Body 602 of implant 600 preferably includes a hollow portion that may be accessed through a cap 614 that is preferably located on an end of implant 600. The hollow portion is adapted to contain fusion promoting material including, but not limited to, bone, in any of its varied forms, hydroxyapatite, coral, bone morphogenetic proteins, genes coding for the production of bone, and agents with the ability to induce cells to become osteoblasts or to make bone.

As shown in FIGS. 50 and 51, a vise 700 has surfaces 702 adapted to cooperatively receive fins 612 and thereby cover the openings between fins 612. While holding implant 600 in vise 700 with cap 614 removed from implant 600, fusion promoting material may be compressively loaded into implant 600. Fusion promoting material may be loaded into implant 600 until the material is extruded from openings in side walls 608.

Having described certain preferred embodiments of the surgical instrument set of the present invention, the method for creating a substantially quadrilateral space in a spine will now be described in more detail. A method for creating a substantially quadrilateral space in a spine for inserting a spinal implant into a disc space between adjacent vertebral bodies, comprises the steps of: positioning guard 170 into contact with the adjacent vertebral bodies for protecting access to the disc base and the adjacent vertebral bodies; and boring, through guard 170, a plurality of bores across the disc space to form the substantially quadrilateral space across the height of the disc space and into the adjacent surfaces of the adjacent vertebral bodies.

The present invention may include the step of marking the spine for guiding, by reference marks, the proper location of guard 170. The step of marking preferably includes inserting a penetrating extension of a spinal marker 100 into a central point of the disc space between the adjacent vertebral bodies. An embodiment of the present invention includes the step of placing dye spots on the spine by injecting the dye through openings in a shaft 102 of spinal marker 100. The depth of penetration of marker 100 into the disc space is controlled.

Yet another embodiment of the method of the present invention includes the step of distracting the disc space between adjacent vertebral bodies, and in particular, the distracting step may include the step of inserting a distractor 130 having a disc penetrating extension into the disc space between adjacent vertebral bodies and against endplates of the adjacent vertebral bodies. The depth of penetration of distractor 130 into the disc space is preferably controlled. The method may further include the step of changing disc penetrating extensions of distractor 130 in accordance with a desired distractor distance between adjacent vertebral bodies. Guard 170 may be inserted over distractor 130 and the disc space, and then distractor 130 may be removed from within guard 170. The positioning step may include inserting at least one disc penetrating extension 176 extending from guard 170 into the disc space between the adjacent vertebral bodies for bearing against endplates of the adjacent vertebral bodies.

The insertion of disc penetrating extension 176 into the disc space in one embodiment of the preferred invention distracts the adjacent vertebral bodies. Another method of the present invention further includes the step of controlling a depth of penetration of extension 176 into the disc space. Another embodiment of the present invention includes the step of engaging guard 170 with the adjacent vertebral bodies through prongs 182 extending from guard 170 and into the adjacent vertebral bodies.

The boring step may include the sub-step of using a template in association with guard 170. The template may be rotated 180 degrees along its longitudinal axis. The boring step may include the sub-step of using either of a drill, mill, laser, or grinder to bore the plurality of bores. The plurality of bores may be overlapping, circular, or both. The boring step may include forming at least three bores in the spine to form a first bore pattern, and in particular may include forming at least a main bore and at least two secondary bores located to a side of the main bore. The main bore has a diameter that is preferably greater than a diameter of each of the two secondary bores. The main bore in the spine is preferably positioned to form a portion of three sides of the substantially quadrilateral space formed in the spine. Each of the two secondary bores are preferably positioned to form a portion of two adjacent sides of the substantially quadrilateral space formed in the spine. A second bore pattern having at least three bores in the spine may be formed such that the first and second bore patterns defined the substantially quadrilateral space. The substantially quadrilateral space may be one of a substantially rectangular shape and a substantially trapezoidal shape.

Further the invention may comprise the step of inserting a multiple passage drill guide 190 into guard 170. Guide 190 may be inserted into guard 170 for guiding the forming of the first bore pattern. The invention may further include the steps of removing guide 190 from guard 170, rotating guide 190 one hundred-eighty degrees along its longitudinal axis, reinserting guide 190 into guard 170, and forming, through the plurality of openings in guide 190, a second bore pattern, the first and second bore patterns defining the substantially quadrilateral space. The invention may further include the step of controlling the depth of penetration of guide 190 into guard 170.

Another embodiment of the present invention includes the step of boring a centralized bore within the substantially quadrilateral space. The centralized bore preferably forms a portion of opposite sides of the substantially quadrilateral space. Further the invention may include the step of inserting a secondary guide 500 into guard 170 and further forming, through an opening in secondary guide 500, a centralized bore within the substantially quadrilateral space.

Yet another embodiment of the present invention includes the step of compressing outer edges of the substantially quadrilateral space. The step of compressing preferably includes inserting a compactor 240 having a compaction end 244 through guard 170 and into the substantially quadrilateral space formed in the spine. The step of compressing preferably includes inserting compactor 240 having compaction end 244 having a sharpened cutting edge for cutting bone. The depth of penetration of compactor 240 into the disc space is preferably controlled. The step of compressing may include the sub step of inserting a spinal implant through guard 170 and into the substantially quadrilateral space formed in the spine to compress the outer edges on the substantially quadrilateral space.

Another embodiment of the present invention includes a surgical method to prepare a segment of a human spine having a disc and two vertebral bodies adjacent the disc for fusion between body portions of the adjacent vertebral bodies and through the space previously occupied by the disc, each of the adjacent vertebral bodies to be fused including a vertebral body having an endplate outer surface adjacent the disc space, and a subchondral zone immediately internal to each endplate, the method comprising: positioning a guard 170 into contact with the adjacent vertebral bodies for protecting access to the disc space and the adjacent vertebral bodies; and forming, through guard 170, a plurality of bores to form a substantially quadrilateral space in the spine across the height of the disc space and into the adjacent endplates of the vertebral bodies adjacent the disc space, the quadrilateral space being formed by the removal of at least bone from at least the adjacent endplates as deep as with, and generally not deeper than, the subchondral zone of each of the adjacent endplates.

Other embodiments of the invention will be apparent to those skilled in the art from consideration of the specification and practice of the invention disclosed herein. It is intended that the specification be considered as exemplary only, and a true scope and spirit of the invention being indicated by the following claims.

What is claimed is:

1. A surgical instrument set for use in spinal surgery for forming a substantially quadrilateral space in the spine for implanting a spinal implant into a disc space between adjacent vertebral bodies, said surgical instrument set comprising:
   a guard having an opening for providing protected access to the disc space and the adjacent surfaces of the vertebral bodies adjacent the disc space, said guard having a proximal end, a distal end, and having a disc penetrating extension extending from said distal end of said guard for insertion into the disc space between the adjacent vertebral bodies, said disc penetrating extension being oriented in a fixed position relative to a central longitudinal axis through said guard and having a portion for bearing against the adjacent vertebral endplates of the adjacent vertebral bodies, said portion of said disc penetrating extension having opposed upper and lower surfaces adapted to bear against each of the adjacent vertebral endplates, respectively, from within the disc space to align the adjacent vertebral bodies, said opening having a minimum cross-sectional dimension perpendicular to the central longitudinal axis, said disc penetrating extension having a maximum height from said upper surface to said lower surface that is greater than a majority of the minimum cross-sectional dimension of said opening; and
   a guide for guiding a bone removal device, said guide having a central longitudinal axis and a shaft adapted to be inserted into said guard, said guide having a perimeter and being configured to guide the formation of a substantially quadrilateral space across the height of the disc space and into the adjacent surfaces of the adjacent vertebral bodies, said guide including a first guide bore having a maximum dimension transverse to and overlapping the central longitudinal axis of said guide, said first guide bore being sized and oriented within said guide to guide the formation of a bore substantially contacting three sides of the substantially quadrilateral space to be formed, said guide including at least a second guide bore having a maximum dimension transverse to the central longitudinal axis of said guide being less than the maximum transverse dimension of said first guide bore, said second guide bore being located between said first guide bore and the perimeter of said guide, said second guide bore being sized and oriented within said guide to guide the formation of a bore substantially contacting two adjacent skies of the substantially quadrilateral space to be formed.

2. The instrument set of claim 1, wherein said guide bores overlap one another.

3. The instrument set of claim 1, wherein at least one of said guide bores is circular.

4. The instrument set of claim 1, further comprising a third guide bore.

5. The instrument set of claim 4, wherein said first guide bore is a main guide bore and said second and third guide bores are secondary guide bores located to a side of said main guide bore.

6. The instrument set of claim 5, wherein said main guide bore has a diameter and said two secondary guide bores have a diameter smaller than the diameter of the main guide bore.

7. The instrument set of claim 6, wherein said main guide bore is sized and oriented within said guide to guide the formation of a bore substantially contacting three sides of the substantially quadrilateral space to be formed.

8. The instrument set of claim 6, wherein each of said two secondary guide bores are sized and oriented within said guide to guide the formation of a bore substantially contacting two adjacent sides of the substantially quadrilateral space to be formed.

9. The instrument set of claim 7, wherein each of said two secondary guide bores are sized and oriented within said guide to guide the formation of a bore substantially contacting two adjacent sides of the substantially quadrilateral space to be formed.

10. The instrument set of claim 9, wherein said main guide bore and said two secondary guide bores are oriented such that the bores formed in the spine through said main guide bore and said two secondary guide bores form a first hole pattern which when said guide is rotated 180 degrees and used to form a second hole pattern the overlapping first and second hole patterns form the substantially quadrilateral space.

11. The instrument set of claim 10, wherein the overlapping first and second hole patterns form one of a substantially rectangular space and a substantially trapezoid space.

12. The instrument set of claim 1, wherein said guide includes means for preventing over penetration of said guide into said guard.

13. The instrument set of claim 12, wherein said preventing means is a trailing end of said guide having a dimension greater than said shaft of said guide.

14. The instrument set of claim 1, wherein said shaft of said guide has one of a rectangular cross-section and a circular cross-section.

15. The instrument set of claim 1, further comprising a secondary guide having a shaft adapted to be inserted into said guard, said secondary guide configured to guide the formation of a bore centrally oriented within the space to be formed.

16. The instrument set of claim 15, wherein said secondary guide is configured to guide the formation of the centrally oriented bore to contact the opposite skies of the substantially quadrilateral space to be formed.

17. The instrument set of claim 1, further comprising a bone compactor having a shaft adapted to be inserted into said guard, said shaft terminating in a compaction end.

18. The instrument set of claim 17, wherein said compaction end has an upper surface and a lower surface for pressing upon the adjacent vertebral endplates of the adjacent vertebral bodies.

19. The instrument set of claim 18, wherein said compaction end has one of a rectangular and trapezoid cross-section.

20. The instrument set of claim 18, wherein said compaction end has a substantially quadrilateral cross-section.

21. The instrument set of claim 17, wherein said compaction end is one of beveled, radiused, and tapered to ease introduction of said bone compactor into the space.

22. The instrument set of claim 17, wherein said shaft of said bone compactor has a trailing end having a dimension greater than said shaft to prevent over penetration of said bone compactor into said guard.

23. The instrument set of claim 17, wherein said shaft of said bone compactor has one of a rectangular cross-section and a circular cross-section.

24. The instrument set of claim 1, wherein said guard has two disc penetrating extensions extending from said guard and diametrically opposed to each other.

25. The instrument set of claim 24, wherein said disc penetrating extensions have a leading edge including one of a pointed, tapered, radiuised, chamfered, and wedge tipped shape to ease insertion of said extensions into the disc space.

26. The instrument set of claim 1, wherein said guard is adapted to conform at least in part to the exterior of the adjacent vertebral bodies.

27. The instrument set of claim 1, wherein said guard includes a shoulder adapted to conform at least in part to the exterior of the adjacent vertebral bodies.

28. The instrument set of claim 27, wherein said shoulder has a curvature configured to correspond to the external curvature of the adjacent vertebral bodies.

29. The instrument set of claim 1, wherein said guard is configured to engage the adjacent vertebral bodies when in use.

30. The instrument set of claim 1, wherein said guard includes a hollow shaft adapted to allow access through said hollow shaft to the disc space.

31. The instrument set of claim 1, further comprising a distractor having a body and a disc penetrating extension extending from said body for insertion into the disc space between adjacent vertebral bodies and for bearing against endplates of the adjacent vertebral bodies.

32. The instrument set of claim 31, wherein said disc penetrating extension is hollow to facilitate insertion of said extension into the disc space.

33. The instrument set of claim 31, wherein said distractor is configured to conform at least in part to the exterior of the adjacent vertebral bodies.

34. The instrument set of claim 31, wherein said distractor includes a shoulder adapted to conform at least in part to the exterior of the adjacent vertebral bodies.

35. The instrument set of claim 34, wherein said shoulder has a curvature configured to correspond to the external curvature of the adjacent vertebral bodies.

36. The instrument set of claim 31, wherein said distractor includes a shaft having one of a rectangular cross-section and a circular cross-section.

37. The instrument set of claim 31, wherein said distractor includes an end for detachably receiving variously sized distractor tips.

38. The instrument set of claim 37, further comprising distractor tips having chisel surfaces.

39. The instrument set of claim 1, further comprising a spinal marker for marking a location on the spine, said marker having a shaft and a disc penetrating extension extending from said shaft for insertion into the disc space between adjacent vertebral bodies.

40. The instrument set of claim 39, wherein said marker includes a shaft having one of a rectangular cross-section and a circular cross-section.

41. The instrument set of claim 39, wherein said marker includes a shoulder for abutting against the exterior of the adjacent vertebral bodies.

42. The instrument set of claim 39, wherein said disc penetrating extension of said marker is tapered to facilitate insertion into the disc space.

43. The instrument set of claim 39, wherein said shaft of said marker has a proximal end and an opposite distal end oriented toward the spine, said shaft of said marker having a passage having a dye receiver at the proximal end of said shaft of said marker and at least one dye exit hole at the distal end of said shaft of said marker for marking the spine.

44. The instrument set of claim 43, wherein said marker is adapted to couple to a syringe.

\* \* \* \* \*

UNITED STATES PATENT AND TRADEMARK OFFICE
CERTIFICATE OF CORRECTION

| | | |
|---|---|---|
| PATENT NO. | : 8,172,853 B2 | Page 1 of 1 |
| APPLICATION NO. | : 10/430783 | |
| DATED | : May 8, 2012 | |
| INVENTOR(S) | : Gary K. Michelson | |

It is certified that error appears in the above-identified patent and that said Letters Patent is hereby corrected as shown below:

Column 20:
Lines 2 and 57, change "skies" to -- sides --.

Column 21:
Line 18, change "radiuised," to -- radiused, --.

Signed and Sealed this
Twenty-fifth Day of December, 2012

David J. Kappos
*Director of the United States Patent and Trademark Office*